(12) United States Patent
Miller et al.

(10) Patent No.: US 9,409,950 B2
(45) Date of Patent: Aug. 9, 2016

(54) LINKER PEPTIDES AND POLYPEPTIDES COMPRISING SAME

(75) Inventors: Brian Robert Miller, San Diego, CA (US); Scott Glaser, San Diego, CA (US); Justin Caravella, Cambridge, MA (US); Susan Foley, Milford, MA (US); Xiaoping Hronowski, Bedford, MA (US); Tigran Aivazian, San Diego, CA (US)

(73) Assignee: Biogen MA Inc., Cambridge, MA (US)

( * ) Notice: Subject to any disclaimer, the term of this patent is extended or adjusted under 35 U.S.C. 154(b) by 288 days.

(21) Appl. No.: 13/996,918

(22) PCT Filed: Dec. 22, 2011

(86) PCT No.: PCT/US2011/066947
§ 371 (c)(1),
(2), (4) Date: Dec. 2, 2013

(87) PCT Pub. No.: WO2012/088461
PCT Pub. Date: Jun. 28, 2012

(65) Prior Publication Data
US 2014/0079701 A1    Mar. 20, 2014

Related U.S. Application Data

(60) Provisional application No. 61/426,993, filed on Dec. 23, 2010.

(51) Int. Cl.
| C07K 7/08 | (2006.01) |
| C07K 16/28 | (2006.01) |
| C07K 16/46 | (2006.01) |
| C12N 15/62 | (2006.01) |
| C07K 16/24 | (2006.01) |

(52) U.S. Cl.
CPC .............. *C07K 7/08* (2013.01); *C07K 16/241* (2013.01); *C07K 16/2875* (2013.01); *C07K 16/468* (2013.01); *C12N 15/62* (2013.01); *C07K 2317/31* (2013.01); *C07K 2317/51* (2013.01); *C07K 2317/622* (2013.01); *C07K 2317/64* (2013.01); *C07K 2317/94* (2013.01); *C07K 2319/00* (2013.01)

(58) Field of Classification Search
CPC .... C07K 7/08; C07K 16/2875; C07K 16/468; C07K 16/241; C07K 2317/52; C07K 2317/569; C07K 2317/94; C07K 2317/31; C07K 2317/622; C07K 2319/00
See application file for complete search history.

(56) References Cited

U.S. PATENT DOCUMENTS

2002/0103353 A1    8/2002  Einat et al.
2008/0219947 A1*   9/2008  Linette et al. ............... 424/85.2

FOREIGN PATENT DOCUMENTS

| WO | 2005/017121 | 2/2005 |
| WO | WO 2007/137279 | 11/2007 |
| WO | WO 2010/010051 | 1/2010 |
| WO | WO 2010/138803 | 12/2010 |

OTHER PUBLICATIONS

Robinson et al., Proc Natl Acad Sci 95: 5929-5934, 1998.*
Volkel et al., Protein Engineering 14(10): 815-823, 2001.*
Jubala et al., Vet Pathol 42: 468-476, 2005.*
Golay et al., Archives of Biochemistry and Biophysics 526: 146-153, 2012.*
Berger et al., N Engl J Med 353: 414-416, Jul. 2005.*
Getts et al., mAbs 2(6): 682-694, 2010.*
Sathish et al., Nature Reviews Drug Discovery 12: 306-324, Apr. 2013.*
International Search Report and Written Opinion in International Application No. PCT/US2011/066947, mailed Oct. 15, 2012, 26 pages.
International Preliminary Report on Patentability in International Application No. PCT/US2011/066947, dated Jun. 25, 2103, 18 pages.
Freund et al., "Characterization of the linker peptide of the single-chain Fv fragment of an antibody by NMR spectroscopy," FEBS, 1993, 320:97-100.
Hoedemaeker et al., "A single chain Fv fragment of P-glycoprotein-specific monoclonal antibody C219. Design, expression, and crystal structure at 2.4 A resolution," J Biol Chem., 1997, 272(47):29784-29789.
Holt et al., "The Genome Sequence of the Malaria Mosquito *Anopheles gambiae*," Sci. Am. Assoc. Adv Sci., Oct. 4, 2003, 298:129-149.
Lu et al., "Bifunctional enhancement of a I-glucanase-xylanase fusion enzyme by optimization of peptide linkers," Appl. Microbiol Biotechnol., Apr. 16, 2008, 79(4):579-587.
Pihkala et al., "An antigen-mediated selection system for mammalian cells that produce glycosylated single-chain Fv," Biochem Biophys Res Comm., Nov. 26, 2004, 324(4):1165-1172.
Roch et al., "Differences in gene expression of human xylosyltransferases and determination of acceptor specificities for various proteoglycans," Biochem Biophys Res Comm., Jan. 2010, 391(1):685-691.
Schouten et al., "Improving scFv antibody expression levels in the plant cytosol," FEBS Lett., Sep. 29, 1997, 41(2):235-241.
Sheridan et al., "A new way to rapidly create functional, fluorescent fusion proteins: random insertion of GFP with an in vitro transposition reaction," BMC Neurosci, BioMed Central, London, Jun. 19, 2002, 3(1):7, 11 pages.
Volkel et al., "Optimized linker sequences for the expression of monomeric and dimeric bispecific single-chain antibodies," Protein Engineering, Oct. 2001, 14(10):815-823.

(Continued)

*Primary Examiner* — Phuong Huynh
(74) *Attorney, Agent, or Firm* — Fish & Richardson P.C.

(57) ABSTRACT

The invention is based, at least in part, on the finding that linker peptides which lack the amino acid sequence GSG reduce or eliminate the addition of posttranslational modifications to the polypeptides which comprise them. More specifically, the novel linker peptides disclosed herein reduce the ability of enzymes to link carbohydrate adducts to polypeptides comprising these linker peptides, e.g., reduce the ability of xylosyltransferase to link xylose to polypeptides. These novel linker peptides, molecules comprising same, and methods of their use are described.

27 Claims, 12 Drawing Sheets

(56) References Cited

OTHER PUBLICATIONS

Wang et al., "Construction of single chain variable fragment (ScFv) and BiscFv-alkaline phosphatase fusion protein for detection of Bacillus anthracis," Anal Chem., Feb. 15, 2006, 78(4):997-1004.

Wang et al., "Enhancement of engineered trifunctional enzyme by optimizing linker peptides for degradation of agricultural by-products," Enzyme Microbial Technol., Oct. 6, 2010, 47(5):194-199.

* cited by examiner

SEQUENCE LISTING

<160> NUMBER OF SEQ ID NOS: 32

<210> SEQ ID NO 1
<211> LENGTH: 15
<212> TYPE: PRT
<213> ORGANISM: Artificial Sequence

```
<220> FEATURE:
<223> OTHER INFORMATION: Synthetic peptide

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: The amino acid group from positions 1 through
      5 may repeat indefinitely.
<220> FEATURE:
<221> NAME/KEY: misc_feature
<222> LOCATION: (4)..(5)
<223> OTHER INFORMATION: Xaa is an amino acid which reduces or
      eliminates the addition of a post-translational modification to
      the polypeptide upon expression in a host cell.

<400> SEQUENCE: 2

Gly Gly Gly Xaa Xaa Gly Gly Gly Gly Ser
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(10)
<223> OTHER INFORMATION: The amino acid group from positions 6 through
      10 may repeat indefinitely.
<220> FEATURE:
<221> NAME/KEY: misc_feature
<222> LOCATION: (6)..(6)
<223> OTHER INFORMATION: Xaa is an amino acid which reduces or
      eliminates the addition of a post-translational modification to
      the polypeptide upon expression in a host cell.

<400> SEQUENCE: 3

Gly Gly Gly Gly Ser Xaa Gly Gly Gly Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: The amino acid group from positions 1 through
      5 may repeat indefinitely.

<400> SEQUENCE: 4

Gly Gly Gly Gly Ala Gly Gly Gly Gly Ser
1               5                   10

<210> SEQ ID NO 5
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 5

Gly Gly Gly Gly Gln Gly Gly Gly Gln Gly Gly Gly Gly Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Gly Gly Gly Pro Ser Gly Gly Gly Pro Ser Gly Gly Gly Gly Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Gly Gly Gly Gly Ser Pro Gly Gly Gly Ser Pro Gly Gly Gly Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Gly Gly Gly Gly Ala Gly Gly Gly Gly Ala Gly Gly Gly Gly Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(15)
<223> OTHER INFORMATION: Any Xaa is an amino acid which reduces or
      eliminates the addition of xylose residues to the linker peptide
      upon expression in a host cell and wherein the linker peptide
      lacks the sequence GSG.

<400> SEQUENCE: 9

Gly Gly Gly Xaa Xaa Gly Gly Gly Xaa Xaa Gly Gly Gly Gly Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(15)
<223> OTHER INFORMATION: Any Xaa is an amino acid which reduces or
      eliminates the addition of xylose residues to the linker peptide
```

-continued upon expression in a host cell and wherein the linker peptide
lacks the sequence GSG.

<400> SEQUENCE: 10

Gly Gly Gly Xaa Xaa Gly Gly Gly Xaa Xaa Gly Gly Gly Xaa Xaa
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(20)
<223> OTHER INFORMATION: Any Xaa is an amino acid which reduces or
      eliminates the addition of xylose residues to the linker peptide
      upon expression in a host cell and wherein the linker peptide
      lacks the sequence GSG.

<400> SEQUENCE: 11

Gly Gly Gly Xaa Xaa Gly Gly Gly Xaa Xaa Gly Gly Gly Xaa Xaa Gly
1               5                   10                  15

Gly Gly Xaa Xaa
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Gly Gly Gly Gly Ala Gly Gly Gly Gly Ala Gly Gly Gly Gly Ala
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Gly Gly Gly Gly Ala Gly Gly Gly Gly Ala Gly Gly Gly Gly Ala Gly
1               5                   10                  15

Gly Gly Gly Ala
            20

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Pro Lys Asn Ser Ser Met Ile Ser Asn Thr Pro
1               5                   10

<210> SEQ ID NO 15
<211> LENGTH: 7
<212> TYPE: PRT
<213> ORGANISM: Artificial Sequence
<220> FEATURE:

```
<223> OTHER INFORMATION: Synthetic peptide

<400> SEQUENCE: 15

His Gln Ser Leu Gly Thr Gln
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

His Gln Asn Leu Ser Asp Gly Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

His Gln Asn Ile Ser Asp Gly Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Val Ile Ser Ser His Leu Gly Gln
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: The amino acid group from positions 1 through
      5 may repeat indefinitely.
<220> FEATURE:
<221> NAME/KEY: misc_feature
<222> LOCATION: (4)..(4)
<223> OTHER INFORMATION: Xaa is Proline
<220> FEATURE:
<221> NAME/KEY: misc_feature
<222> LOCATION: (5)..(5)
<223> OTHER INFORMATION: Xaa is Serine

<400> SEQUENCE: 19

Gly Gly Gly Xaa Xaa Gly Gly Gly Gly Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide
```

-continued

<220> FEATURE:
<221> NAME/KEY: misc_feature
<222> LOCATION: (1)..(5)
<223> OTHER INFORMATION: The amino acid group from positions 1 through 5 may repeat indefinitely.
<220> FEATURE:
<221> NAME/KEY: misc_feature
<222> LOCATION: (4)..(4)
<223> OTHER INFORMATION: Xaa is Gly
<220> FEATURE:
<221> NAME/KEY: misc_feature
<222> LOCATION: (5)..(5)
<223> OTHER INFORMATION: Xaa is Gln

<400> SEQUENCE: 20

Gly Gly Gly Xaa Xaa Gly Gly Gly Gly Ser
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: The amino acid group from positions 1 through 5 may repeat indefinitely.
<220> FEATURE:
<221> NAME/KEY: misc_feature
<222> LOCATION: (4)..(4)
<223> OTHER INFORMATION: Xaa is Gly
<220> FEATURE:
<221> NAME/KEY: misc_feature
<222> LOCATION: (5)..(5)
<223> OTHER INFORMATION: Xaa is Ala

<400> SEQUENCE: 21

Gly Gly Gly Xaa Xaa Gly Gly Gly Gly Ser
1 5 10

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 22

Gly Gly Gly Gly Ser Xaa Gly Gly Gly Ser Xaa Gly Gly Gly Ser
1 5 10 15

<210> SEQ ID NO 23
<211> LENGTH: 219
<212> TYPE: PRT
<213> ORGANISM: Artificial Sequence
<220> FEATURE:
<223> OTHER INFORMATION: Synthetic peptide: Light Chain of XWU198 TNF-TWEAK

<400> SEQUENCE: 23

Asp Val Val Met Thr Gln Ser Pro Leu Ser Leu Pro Val Thr Pro Gly
1 5 10 15

```
Glu Pro Ala Ser Ile Ser Cys Arg Ser Ser Gln Ser Leu Val Ser Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Arg Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 24
<211> LENGTH: 719
<212> TYPE: PRT
<213> ORGANISM: Artificial Sequence
<220> FEATURE:
<223> OTHER INFORMATION: Synthetic peptide: Heavy Chain + scFv of
      XWU198 TNF-TWEAK for traditional G/S linkers

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu Val Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
```

-continued

```
            145                 150                 155                 160
        Pro Val Thr Val Ser Trp Asn Ser Gly Ala Leu Thr Ser Gly Val His
                        165                 170                 175
        Thr Phe Pro Ala Val Leu Gln Ser Ser Gly Leu Tyr Ser Leu Ser Ser
                        180                 185                 190
        Val Val Thr Val Pro Ser Ser Leu Gly Thr Gln Thr Tyr Ile Cys
                        195                 200                 205
        Asn Val Asn His Lys Pro Ser Asn Thr Lys Val Asp Lys Lys Val Glu
                        210                 215                 220
        Pro Lys Ser Cys Asp Lys Thr His Thr Cys Pro Pro Cys Pro Ala Pro
        225                 230                 235                 240
        Glu Leu Leu Gly Gly Pro Ser Val Phe Leu Phe Pro Pro Lys Pro Lys
                        245                 250                 255
        Asp Thr Leu Met Ile Ser Arg Thr Pro Glu Val Thr Cys Val Val Val
                        260                 265                 270
        Asp Val Ser His Glu Asp Pro Glu Val Lys Phe Asn Trp Tyr Val Asp
                        275                 280                 285
        Gly Val Glu Val His Asn Ala Lys Thr Lys Pro Arg Glu Glu Gln Tyr
                        290                 295                 300
        Asn Ser Thr Tyr Arg Val Val Ser Val Leu Thr Val Leu His Gln Asp
        305                 310                 315                 320
        Trp Leu Asn Gly Lys Glu Tyr Lys Cys Lys Val Ser Asn Lys Ala Leu
                        325                 330                 335
        Pro Ala Pro Ile Glu Lys Thr Ile Ser Lys Ala Lys Gly Gln Pro Arg
                        340                 345                 350
        Glu Pro Gln Val Tyr Thr Leu Pro Pro Ser Arg Asp Glu Leu Thr Lys
                        355                 360                 365
        Asn Gln Val Ser Leu Thr Cys Leu Val Lys Gly Phe Tyr Pro Ser Asp
                        370                 375                 380
        Ile Ala Val Glu Trp Glu Ser Asn Gly Gln Pro Glu Asn Asn Tyr Lys
        385                 390                 395                 400
        Thr Thr Pro Pro Val Leu Asp Ser Asp Gly Ser Phe Phe Leu Tyr Ser
                        405                 410                 415
        Lys Leu Thr Val Asp Lys Ser Arg Trp Gln Gln Gly Asn Val Phe Ser
                        420                 425                 430
        Cys Ser Val Met His Glu Ala Leu His Asn His Tyr Thr Gln Lys Ser
                        435                 440                 445
        Leu Ser Leu Ser Pro Gly Lys Ser Gly Gly Gly Ser Gly Gly Gly
                        450                 455                 460
        Gly Ser Gly Gly Gly Ser Glu Val Gln Leu Val Glu Ser Gly Gly
        465                 470                 475                 480
        Gly Leu Val Gln Pro Gly Gly Ser Leu Arg Leu Ser Cys Ala Ala Ser
                        485                 490                 495
        Gly Phe Thr Phe Ser Asp Tyr Ala Met His Trp Val Arg Gln Ala Pro
                        500                 505                 510
        Gly Lys Gly Leu Glu Trp Val Ser Ala Ile Ser Trp Asn Ser Gly His
                        515                 520                 525
        Ile Asp Tyr Ala Asp Ser Val Glu Gly Arg Phe Thr Ile Ser Arg Asp
                        530                 535                 540
        Asn Ala Lys Asn Ser Leu Tyr Leu Gln Met Asn Ser Leu Arg Ala Glu
        545                 550                 555                 560
        Asp Thr Ala Val Tyr Tyr Cys Ala Lys Val Ser Tyr Leu Ser Thr Ala
                        565                 570                 575
```

```
Ser Ser Leu Asp Tyr Trp Gly Gln Gly Thr Leu Val Thr Val Ser Ser
            580                 585                 590

Gly Gly Gly Gly Ser Gly Gly Gly Gly Ser Gly Gly Gly Gly Ser Gly
            595                 600                 605

Gly Gly Gly Ser Asp Ile Gln Met Thr Gln Ser Pro Ser Ser Leu Ser
            610                 615                 620

Ala Ser Val Gly Asp Arg Val Thr Ile Thr Cys Arg Ala Ser Gln Gly
625                 630                 635                 640

Ile Arg Asn Tyr Leu Ala Trp Tyr Gln Gln Lys Pro Gly Lys Ala Pro
                645                 650                 655

Lys Leu Leu Ile Tyr Ala Ala Ser Thr Arg Gln Ser Gly Val Pro Ser
                660                 665                 670

Arg Phe Ser Gly Ser Gly Ser Gly Thr Asp Phe Thr Leu Thr Ile Ser
                675                 680                 685

Ser Leu Gln Pro Glu Asp Glu Ala Thr Tyr Tyr Cys Gln Arg Tyr Asn
            690                 695                 700

Arg Ala Pro Tyr Thr Phe Gly Gln Gly Thr Lys Val Glu Ile Lys
705                 710                 715

<210> SEQ ID NO 25
<211> LENGTH: 718
<212> TYPE: PRT
<213> ORGANISM: Artificial Sequence
<220> FEATURE:
<223> OTHER INFORMATION: Synthetic peptide: Heavy Chain + scFv of
      BRM074 TNF-TWEAK for Test 074

<400> SEQUENCE: 25

Glu Val Gly Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu Val Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
```

```
                  210                 215                 220
Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                    260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys Ser Gly Gly Ala Gly Gly Gly Gly
        450                 455                 460

Ala Gly Gly Gly Ser Glu Val Gln Leu Val Glu Ser Gly Gly Gly
465                 470                 475                 480

Leu Val Gln Pro Gly Gly Ser Leu Arg Leu Ser Cys Ala Ala Ser Gly
                485                 490                 495

Phe Thr Phe Ser Asp Tyr Ala Met His Trp Val Arg Gln Ala Pro Gly
                500                 505                 510

Lys Gly Leu Glu Trp Val Ser Ala Ile Ser Trp Asn Ser Gly His Ile
            515                 520                 525

Asp Tyr Ala Asp Ser Val Glu Gly Arg Phe Thr Ile Ser Arg Asp Asn
        530                 535                 540

Ala Lys Asn Ser Leu Tyr Leu Gln Met Asn Ser Leu Arg Ala Glu Asp
545                 550                 555                 560

Thr Ala Val Tyr Tyr Cys Ala Lys Val Ser Tyr Leu Ser Thr Ala Ser
                565                 570                 575

Ser Leu Asp Tyr Trp Gly Gln Gly Thr Leu Val Thr Val Ser Ser Gly
            580                 585                 590

Gly Gly Gly Ser Gly Gly Gly Gly Ser Gly Gly Gly Gly Ser Gly Gly
        595                 600                 605

Gly Gly Ser Asp Ile Gln Met Thr Gln Ser Pro Ser Ser Leu Ser Ala
    610                 615                 620

Ser Val Gly Asp Arg Val Thr Ile Thr Cys Arg Ala Ser Gln Gly Ile
625                 630                 635                 640
```

-continued

```
Arg Asn Tyr Leu Ala Trp Tyr Gln Gln Lys Pro Gly Lys Ala Pro Lys
            645                 650                 655

Leu Leu Ile Tyr Ala Ala Ser Thr Arg Gln Ser Gly Val Pro Ser Arg
        660                 665                 670

Phe Ser Gly Ser Gly Ser Gly Thr Asp Phe Thr Leu Thr Ile Ser Ser
    675                 680                 685

Leu Gln Pro Glu Asp Glu Ala Thr Tyr Tyr Cys Gln Arg Tyr Asn Arg
690                 695                 700

Ala Pro Tyr Thr Phe Gly Gln Gly Thr Lys Val Glu Ile Lys
705                 710                 715

<210> SEQ ID NO 26
<211> LENGTH: 718
<212> TYPE: PRT
<213> ORGANISM: Artificial Sequence
<220> FEATURE:
<223> OTHER INFORMATION: Synthetic peptide: Heavy Chain + scFv of
      BRM075 TNF-TWEAK for Test 075

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Asp Gly Asp Arg Ile Glu Val Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Ile Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
```

-continued

```
               275                 280                 285
Val Glu Val His Asn Ala Lys Thr Lys Pro Arg Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys Ser Gly Gly Gly Gln Gly Gly Gly Gly
450                 455                 460

Gln Gly Gly Gly Gly Ser Glu Val Gln Leu Val Glu Ser Gly Gly Gly
465                 470                 475                 480

Leu Val Gln Pro Gly Gly Ser Leu Arg Leu Ser Cys Ala Ala Ser Gly
                485                 490                 495

Phe Thr Phe Ser Asp Tyr Ala Met His Trp Val Arg Gln Ala Pro Gly
                500                 505                 510

Lys Gly Leu Glu Trp Val Ser Ala Ile Ser Trp Asn Ser Gly His Ile
                515                 520                 525

Asp Tyr Ala Asp Ser Val Glu Gly Arg Phe Thr Ile Ser Arg Asp Asn
530                 535                 540

Ala Lys Asn Ser Leu Tyr Leu Gln Met Asn Ser Leu Arg Ala Glu Asp
545                 550                 555                 560

Thr Ala Val Tyr Tyr Cys Ala Lys Val Ser Tyr Leu Ser Thr Ala Ser
                565                 570                 575

Ser Leu Asp Tyr Trp Gly Gln Gly Thr Leu Val Thr Val Ser Ser Gly
                580                 585                 590

Gly Gly Gly Ser Gly Gly Gly Gly Ser Gly Gly Gly Gly Ser Gly Gly
                595                 600                 605

Gly Gly Ser Asp Ile Gln Met Thr Gln Ser Pro Ser Ser Leu Ser Ala
                610                 615                 620

Ser Val Gly Asp Arg Val Thr Ile Thr Cys Arg Ala Ser Gln Gly Ile
625                 630                 635                 640

Arg Asn Tyr Leu Ala Trp Tyr Gln Gln Lys Pro Gly Lys Ala Pro Lys
                645                 650                 655

Leu Leu Ile Tyr Ala Ala Ser Thr Arg Gln Ser Gly Val Pro Ser Arg
                660                 665                 670

Phe Ser Gly Ser Gly Ser Gly Thr Asp Phe Thr Leu Thr Ile Ser Ser
                675                 680                 685

Leu Gln Pro Glu Asp Glu Ala Thr Tyr Tyr Cys Gln Arg Tyr Asn Arg
                690                 695                 700
```

Ala Pro Tyr Thr Phe Gly Gln Gly Thr Lys Val Glu Ile Lys
705                 710                 715

<210> SEQ ID NO 27
<211> LENGTH: 719
<212> TYPE: PRT
<213> ORGANISM: Artificial Sequence
<220> FEATURE:
<223> OTHER INFORMATION: Synthetic peptide: Heavy Chain + scFv of
      BRM076 TNF-TWEAK for Test 076

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Pro Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Tyr Tyr Asp Tyr Gly Asp Arg Ile Glu Val Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Ile Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg

```
                  340                 345                 350
Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Ile Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Ser Gly Gly Gly Pro Ser Gly Gly Gly
    450                 455                 460

Pro Ser Gly Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Phe Thr Phe Ser Asp Tyr Ala Met His Trp Val Arg Gln Ala Pro
            500                 505                 510

Gly Lys Gly Leu Glu Trp Val Ser Ala Ile Ser Trp Asn Ser Gly His
        515                 520                 525

Ile Asp Tyr Ala Asp Ser Val Glu Gly Arg Phe Thr Ile Ser Arg Asp
    530                 535                 540

Asn Ala Lys Asn Ser Leu Tyr Leu Gln Met Asn Ser Leu Arg Ala Glu
545                 550                 555                 560

Asp Thr Ala Val Tyr Tyr Cys Ala Lys Val Ser Tyr Leu Ser Thr Ala
                565                 570                 575

Ser Ser Leu Asp Tyr Trp Gly Gln Gly Thr Leu Val Thr Val Ser Ser
            580                 585                 590

Gly Gly Gly Gly Ser Gly Gly Gly Ser Gly Gly Gly Gly Ser Gly
        595                 600                 605

Gly Gly Gly Ser Asp Ile Gln Met Thr Gln Ser Pro Ser Ser Leu Ser
    610                 615                 620

Ala Ser Val Gly Asp Arg Val Thr Ile Thr Cys Arg Ala Ser Gln Gly
625                 630                 635                 640

Ile Arg Asn Tyr Leu Ala Trp Tyr Gln Gln Lys Pro Gly Lys Ala Pro
                645                 650                 655

Lys Leu Leu Ile Tyr Ala Ala Ser Thr Arg Gln Ser Gly Val Pro Ser
            660                 665                 670

Arg Phe Ser Gly Ser Gly Ser Gly Thr Asp Phe Thr Leu Thr Ile Ser
        675                 680                 685

Ser Leu Gln Pro Glu Asp Glu Ala Thr Tyr Tyr Cys Gln Arg Tyr Asn
    690                 695                 700

Arg Ala Pro Tyr Thr Phe Gly Gln Gly Thr Lys Val Glu Ile Lys
705                 710                 715

<210> SEQ ID NO 28
<211> LENGTH: 718
<212> TYPE: PRT
<213> ORGANISM: Artificial Sequence
<220> FEATURE:
<223> OTHER INFORMATION: Synthetic peptide: Heavy Chain + sdFv of
      BRM077 TNF-TWEAK for Test 077
```

<400> SEQUENCE: 28

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
             20                  25                  30

Ala Met Ser Trp Val Arg Gln Ala Pro Gly Lys Gly Leu Glu Trp Val
         35                  40                  45

Ala Glu Ile Ser Ser Gly Gly Ser Tyr Pro Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Tyr Tyr Asp Tyr Asp Gly Asp Arg Ile Glu Val Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Phe Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
```

```
            405                 410                 415
Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys Ser Gly Gly Ser Pro Gly Gly Gly
        450                 455                 460

Ser Pro Gly Gly Ser Glu Val Gln Leu Val Glu Ser Gly Gly Gly
465                 470                 475                 480

Leu Val Gln Pro Gly Gly Ser Leu Arg Leu Ser Cys Ala Ala Ser Gly
                485                 490                 495

Phe Thr Phe Ser Asp Tyr Ala Met His Trp Val Arg Gln Ala Pro Gly
            500                 505                 510

Lys Gly Leu Glu Trp Val Ser Ala Ile Ser Trp Asn Ser Gly His Ile
        515                 520                 525

Asp Tyr Ala Asp Ser Val Glu Gly Arg Phe Thr Ile Ser Arg Asp Asn
        530                 535                 540

Ala Lys Asn Ser Leu Tyr Leu Gln Met Asn Ser Leu Arg Ala Glu Asp
545                 550                 555                 560

Thr Ala Val Tyr Tyr Cys Ala Lys Val Ser Tyr Leu Ser Thr Ala Ser
                565                 570                 575

Ser Leu Asp Tyr Trp Gly Gln Gly Thr Leu Val Thr Val Ser Ser Gly
            580                 585                 590

Gly Gly Gly Ser Gly Gly Gly Gly Ser Gly Gly Gly Gly Ser Gly Gly
                595                 600                 605

Gly Gly Ser Asp Ile Gln Met Thr Gln Ser Pro Ser Ser Leu Ser Ala
        610                 615                 620

Ser Val Gly Asp Arg Val Thr Ile Thr Cys Arg Ala Ser Gln Gly Ile
625                 630                 635                 640

Arg Asn Tyr Leu Ala Trp Tyr Gln Gln Lys Pro Gly Lys Ala Pro Lys
                645                 650                 655

Leu Leu Ile Tyr Ala Ala Ser Thr Arg Gln Ser Gly Val Pro Ser Arg
            660                 665                 670

Phe Ser Gly Ser Gly Ser Gly Thr Asp Phe Thr Leu Thr Ile Ser Ser
        675                 680                 685

Leu Gln Pro Glu Asp Glu Ala Thr Tyr Tyr Cys Gln Arg Tyr Asn Arg
        690                 695                 700

Ala Pro Tyr Thr Phe Gly Gln Gly Thr Lys Val Glu Ile Lys
705                 710                 715

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Gly Gly Gly Gly Ser Gly Gly Gly Gly Ser Gly Gly Gly Gly Ser Gly
1               5                   10                  15

Gly Gly Gly Ser
            20

<210> SEQ ID NO 30
<211> LENGTH: 5
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: The amino acid group from positions 1 through
      5 may repeat indefinitely.

<400> SEQUENCE: 30

Gly Gly Gly Gly Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Any Xaa can be Asp or Glu

<400> SEQUENCE: 31

Xaa Gly Ser Gly Xaa
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: The amino acid group from positions 1 through
      5 may repeat indefinitely.

<400> SEQUENCE: 32

Gly Gly Gly Gly Ser
1               5
```

US 9,409,950 B2

LINKER PEPTIDES AND POLYPEPTIDES COMPRISING SAME

RELATED APPLICATIONS

This application is a 35 U.S.C. 371 national stage filing of International Application No. PCT/US2011/066947, filed on Dec. 22, 2011, which claims priority to U.S. Provisional Application No. 61/426,993, filed on Dec. 23, 2010. The contents of the aforementioned applications are hereby incorporated by reference.

BACKGROUND OF THE INVENTION

The application of protein engineering techniques to fusion protein design has produced a number of formats that have been shown to have altered, and in some cases, improved pharmacodynamic, biodistribution, and activity profiles. Linker peptides are frequently an important part of these constructs.

Linker peptides are synthetic sequences of amino acids that are commonly used to physically connect polypeptide domains. Most linker peptides are composed of repetitive modules of one or more of the amino acids glycine and serine. The standard 15 amino acid $(GGGGS)_3$ linker peptide has been well-characterized (e.g., within the context of an antibody single-chain Fv (scFv) domain) and has been shown to adopt an unstructured, flexible conformation. In addition, this linker peptide does not interfere with assembly and binding activity of the domains it connects. (Freund, C. et al., 1993. FEBS 320:97).

Unfortunately, when polypeptide constructs comprising linker peptides are expressed in a host cell, the linker peptides can serve as substrates for post-translational modification. Such post-translational modification can create heterogeneity in the protein product produced. Thus, new linker peptides that reduce or eliminate the addition of post-translational modifications would enable the production of more homogenous polypeptide preparations; such homogeneous preparations are critical for clinically relevant polypeptides.

SUMMARY OF THE INVENTION

The invention is based, at least in part, on the finding that linker peptides which lack the amino acid sequence GSG reduce or eliminate the addition of post-translational modifications to the polypeptides which comprise them. More specifically, the novel linker peptides disclosed herein reduce the ability of enzymes to link carbohydrate adducts to polypeptides comprising these linker peptides, e.g., reduce the ability of xylosyltransferase to link xylose to polypeptides. Surprisingly, this is true even though the amino acid sequence GSG alone was not previously thought to be sufficient for xylosyltransferase-mediated addition of xylose to proteins. Moreover, polypeptides comprising the linker peptides of the invention have been found to exhibit reduced aggregation and increased pH stability. Thus, the inclusion of the linker peptides of the invention in polypeptide molecules leads to increased homogeneity, increased pH stability and reduced aggregation.

Accordingly, in one aspect, the invention pertains to a polypeptide comprising a linker peptide, wherein the linker peptide lacks the sequence GSG and comprises an amino acid sequence selected from the group consisting of $(GGGXX)_n$ GGGGS and $GGGGS(XGGGS)_n$, wherein n is greater than or equal to 1, and wherein X is an amino acid which reduces or eliminates the addition of a post-translational modification to the polypeptide upon expression in a host cell.

In one embodiment, the post-translational modification is the addition of a carbohydrate adduct. In one embodiment, the carbohydrate adduct is a xylose adduct.

In one embodiment, the linker peptide comprises the amino acid sequence $(GGGGA)_n GGGGS$. In another embodiment, the linker peptide comprises the amino acid sequence $(GGGGQ)_2 GGGGS$. In yet another embodiment, the linker peptide comprises the amino acid sequence $(GGGPS)_2 GGGGS$. In still another embodiment, the linker peptide comprises the amino acid sequence $GGGGS(PGGGS)_2$. In a further embodiment, the linker peptide consists of the amino acid sequence $(GGGGA)_2 GGGGS$. In another embodiment, the linker peptide consists of the amino acid sequence $(GGGGQ)_2 GGGGS$. In another embodiment, the linker peptide consists of the amino acid sequence $(GGGPS)_2 GGGGS$. In another embodiment, the linker peptide consists of the amino acid sequence $GGGGS(PGGGS)_2$.

In one embodiment, the linker peptide is genetically fused to an Fc moiety or Fc region, e.g., an scFc region.

In one embodiment, at least one copy of the linker peptide is interposed between two polypeptide domains, wherein at least one of the polypeptide domains comprises a biologically active moiety.

In one embodiment, the biologically active moiety is selected from the group consisting of: a VH domain, a VL domain, an scFv molecule, an Fc moiety, a receptor or extracellular domain thereof, an Fab, and a receptor binding portion of a ligand, an enzyme, a growth factor, an interleukin, a cytokine, and a chemokine.

In one embodiment, the Fc moiety is an Fc region.
In one embodiment, the Fc moiety is an scFc region.
In another embodiment, the polypeptide is a bispecific antibody molecule.

In one aspect, the invention pertains to a composition comprising a polypeptide comprising a linker peptide of the invention and a pharmaceutically acceptable carrier.

In another embodiment, the invention pertains to a nucleic acid molecule encoding a polypeptide comprising a linker peptide of the invention. In one embodiment, the nucleic acid molecule is in a vector. In another embodiment, the invention pertains to a host cell comprising the nucleic acid molecule of the invention.

In one aspect, the invention pertains to a binding molecule comprising an scFv moiety and an Fc moiety, wherein the scFv moiety and the Fc moiety are genetically linked by a linker peptide, wherein the linker peptide comprises the amino acid sequence $(GGGXX)_2 GGGGS$, wherein X is an amino acid which reduces or eliminates the addition of xylose residues to the linker peptide upon expression in a host cell and wherein the linker peptide lacks the sequence GSG.

In one embodiment, the invention pertains to a binding molecule of claim 22, wherein the scFv moiety and the Fc moiety are genetically linked by a linker peptide selected from the group consisting of $(GGGGA)_2 GGGGS$ and $(GGGGQ)_2 GGGGS$.

In another embodiment, the invention pertains to a composition comprising a binding molecule of the invention and a pharmaceutically acceptable carrier.

In another aspect, the invention pertains to an scFv molecule comprising a VH and a VL region, wherein the VH and VL region are genetically linked by a linker peptide, wherein the linker peptide comprises the amino acid sequence $(GGGXX)_3$ or $(GGGXX)_4$, wherein X is an amino acid which reduces or eliminates the addition of xylose residues to the linker peptide upon expression in a host cell and wherein the linker peptide lacks the sequence GSG.

In another embodiment, the invention pertains to an scFv molecule wherein the VH and the VL region are genetically linked by a linker peptide comprising the amino acid sequence selected from the group consisting of (GGGGA)$_3$ and (GGGGA)$_4$.

In another aspect, the invention pertains to a binding molecule comprising an scFv moiety which comprises a VH and a VL region and an Fc moiety, wherein the scFv moiety and the Fc moiety are genetically linked by a linker peptide comprising the amino acid sequence (GGGGA)$_2$GGGGS and the VH and the VL region are genetically linked by a linker peptide comprising the amino acid sequence (GGGGS)$_4$.

In a further aspect, the invention pertains to a binding molecule comprising an scFv moiety which comprises a VH and a VL region and an Fc moiety, wherein the scFv moiety and the Fc moiety are genetically linked by a linker peptide comprising the amino acid sequence (GGGGS)$_3$ and the VH and the VL region are genetically linked by a linker peptide comprising the amino acid sequence (GGGGA)$_4$.

In yet another embodiment, the invention pertains to a binding molecule comprising an scFv moiety which comprises a VH and a VL region and an Fc moiety, wherein the scFv moiety and the Fc moiety are genetically linked by a linker peptide comprising the amino acid sequence (GGGGA)$_2$GGGGS and the VH and the VL region are genetically linked by a linker peptide comprising the amino acid sequence (GGGGA)$_4$.

In another embodiment, the invention pertains to a linker peptide comprising the amino acid sequence (GGGGA)$_2$GGGGS.

In another embodiment, the invention pertains to a linker peptide comprising the amino acid sequence GGGGS (PGGGS)$_2$.

In another embodiment, the invention pertains to a linker peptide consisting of the amino acid sequence (GGGGA)$_2$GGGGS.

In another embodiment, the invention pertains to a linker peptide consisting of the amino acid sequence (GGGGQ)$_2$GGGGS.

In another embodiment, the invention pertains to a linker peptide consisting of the amino acid sequence (GGGPS)$_2$GGGGS.

In another embodiment, the invention pertains to a linker peptide consisting of the amino acid sequence GGGGS (PGGGS)2.

In another aspect, the invention pertains to a method of making a polypeptide having reduced levels of xylose residues comprising culturing the host cell of the invention under conditions where the fusion protein is expressed and recovering the fusion protein from the medium, to thereby make a fusion protein having reduced levels of xylose residues.

In another aspect, the invention pertains to a method of making a stabilized polypeptide comprising genetically engineering a fusion protein to comprise a linker peptide of the invention and causing the fusion protein to be expressed by a cell, to thereby make a stabilized polypeptide.

In another aspect, the invention pertains to a method of treating a subject that would benefit from treatment with a fusion protein comprising administering a composition of the invention to the subject.

In yet another embodiment, the invention pertains to use of a composition of the invention for the treatment of a disease or disorder.

In addition, in one embodiment, the invention pertains to polypeptide molecules comprising one or more of the linkers present in the test 074, 075, 076, and 077 molecules described in the Examples (SEQ ID Nos 8, 5, 6, and 7, respectively).

In another embodiment, the invention pertains to the test molecules 074, 075, 076, and 077 described in the Examples (SEQ ID Nos 25-28, respectively).

DETAILED DESCRIPTION OF THE INVENTION

Figure 1:
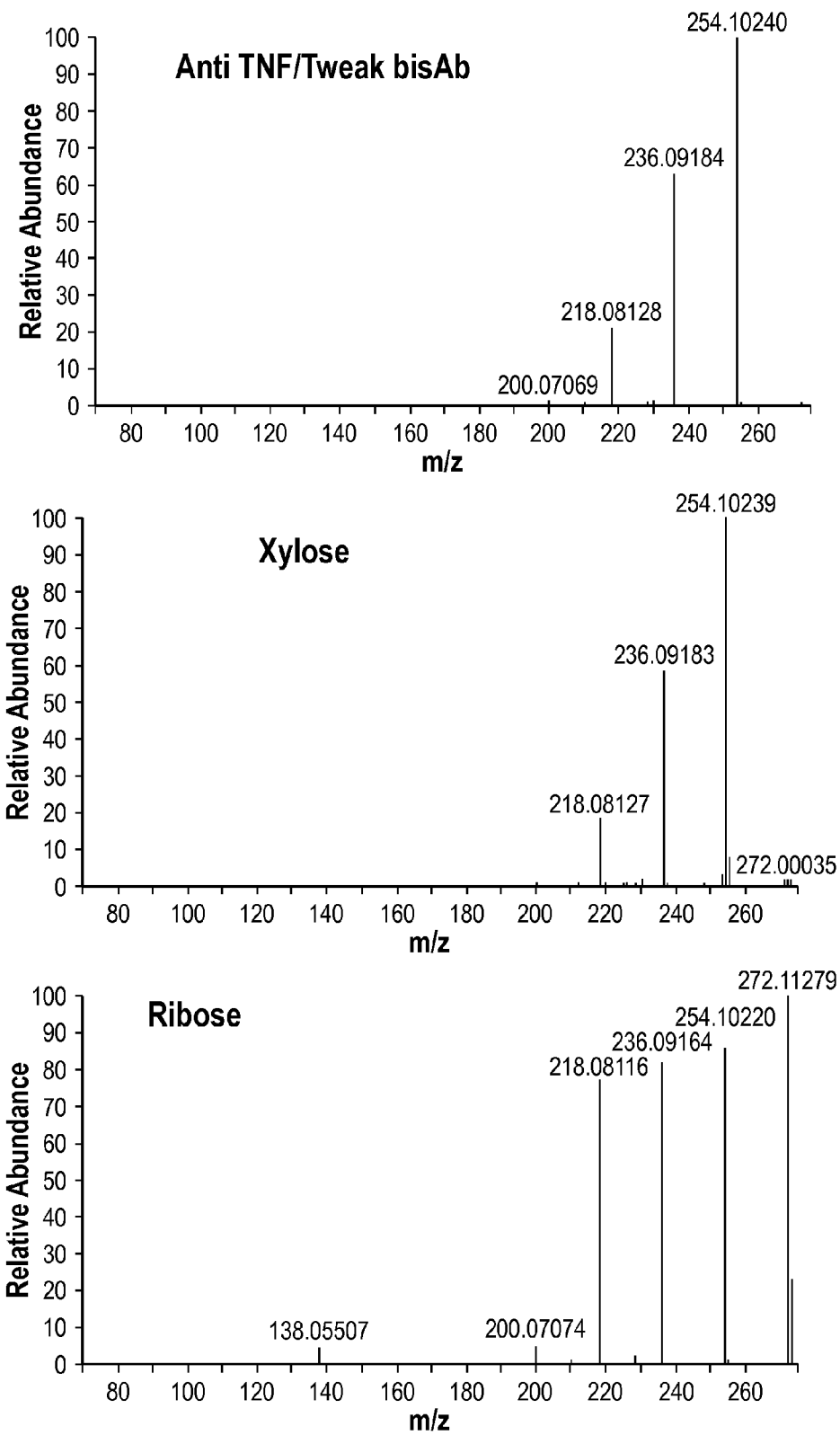
FIG. 1 shows analysis of the regimentation pattern observed by FT MS/MS revealed that a bispecific antibody comprising a traditional gly-ser linker closely resembled that of the xylose standard, and was clearly different from the ribose standard.

Homogeneity of manufactured proteins is extremely important if those proteins are to be used clinically. Surprisingly, as demonstrated herein, alteration of the amino acid sequence of linker peptides incorporated into polypeptides has been found to reduce or eliminate the addition of xylose residues on serine residues present in the linker peptide. Reduction or elimination of post-translationally added xylose residues improves polypeptide homogeneity. This is so even though the amino acid sequence GSG is not the complete motif thought to be recognized by xylosyltransferase. In addition, inclusion of these same linkers further improves the quality of polypeptides by increasing pH stability and reducing the levels of aggregated protein product.

Before further description of the invention, for convenience, certain terms are described below:

1. Definitions

As used herein, the term "protein" or "polypeptide" refers to a polymer of two or more of the natural amino acids or non-natural amino acids.

The term "amino acid" includes alanine (Ala or A); arginine (Arg or R); asparagines (Asn or N); aspartic acid (Asp or D); cysteine (Cys or C); glutamine (Gln or Q); glutamic acid (Glu or E); glycine (Gly or G); histidine (H is or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" include amino acids that can have non-zero net charge on their side chains (e.g. R, K, H, E, D). These amino acids can participate in hydrophobic interactions and electrostatic interactions.

As used herein the term "linker peptide" refers to synthetic amino acid sequences that connect or link two polypeptide sequences, e.g., that link two polypeptide domains. As used herein the term "synthetic" refers to amino acid sequences that are not naturally occurring.

Linker peptides of the invention connect two amino acid sequences via peptide bonds. In one embodiment, a linker peptide of the invention connects a biologically active moiety to a second moiety in a linear sequence. In another embodiment, a linker peptide connects two biologically active moieties.

In the context of polypeptides, a "linear sequence" or a "sequence" is the order of amino acids in a polypeptide in an amino to carboxyl terminal direction in which residues that neighbor each other in the sequence are contiguous in the primary structure of the polypeptide.

As used herein, the terms "linked," "fused", or "fusion", are used interchangeably. These terms refer to the joining together of two more elements or components, by whatever means including chemical conjugation or recombinant means. Methods of chemical conjugation (e.g., using heterobifunctional crosslinking agents) are known in the art. As used herein, the term "genetically fused," "genetically linked" or "genetic fusion" refers to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

The linker peptides of the instant invention differ from traditional Gly/Ser (GS) linker peptides of the art in that the presently claimed linker peptides lack the amino acid sequence GSG. As used herein, the term "gly-ser linker" or "linker peptide" refers to a peptide that consists of glycine and serine residues. An exemplary gly/ser polypeptide linker comprises the amino acid sequence (Gly4 Ser)n. In one embodiment, linker peptide of the instant invention comprises or consists of a Gly/Ser linker peptide with one or more amino acid substitutions, deletions, and/or additions and which lacks the amino acid sequence GSG.

In another embodiment, a linker peptide of the invention comprises or consists of the amino acid sequence $(GGGXX)_n$ GGGGS or $GGGGS(XGGGS)_n$, where n is greater than or equal to one. In one embodiment, n is between 1 and 20, inclusive. In one embodiment, n=1. In one embodiment, n=2. In another embodiment, n=3. In another embodiment, n=4. In another embodiment, n=5. In yet another embodiment, n=6. In another embodiment, n=7. In yet another embodiment, n=8. In another embodiment, n=9. In yet another embodiment, n=10.

In addition to comprising one or more novel linker peptide(s) of the invention, in certain embodiments, a polypeptide may comprise one or more traditional Gly/Ser linker peptides at other locations within the polypeptide.

As used herein, the term "post translational modification" includes modifications made to polypeptides after translation. Examples of post translational modification include, for example, the attachment of functional groups such as acetate, phosphate, lipids, or carbohydrates or phosphate groups to the polypeptide in a cell. The addition of functional groups is generally triggered by the presence of consensus motifs in the polypeptide.

The term "glycosylation" refers to the covalent linking of one or more carbohydrate adducts to a polypeptide. The term "carbohydrate adduct" refers to a carbohydrate moiety which is enzymatically linked to a polypeptide. Typically, glycosylation is a posttranslational event which can occur within the intracellular milieu of a cell or extract therefrom. The term glycosylation includes, for example, addition of a sugar residue at a consensus site for glycosylation. One example of glycosylation involves the addition of one or more xylose adducts to a polypeptide. For example, the consensus sequence for xylose addition comprises the sequence [DIE GSG DIE]. The second acidic amino acid (D/E) is required for chain extension.

The subject polypeptides comprise at least one biologically active moiety. A biologically active moiety refers to a moiety capable of one or more of: localizing or targeting a molecule to a desired site or cell, performing a function, performing an action or a reaction in a biological context. For example, the term "biologically active moiety" refers to biologically active molecules or portions thereof which bind to components of a biological system (e.g., proteins in sera or on the surface of cells or in cellular matrix) and which binding results in a biological effect (e.g., as measured by a change in the active moiety and/or the component to which it binds (e.g., a cleavage of the active moiety and/or the component to which it binds, the transmission of a signal, or the augmentation or inhibition of a biological response in a cell or in a subject)).

Exemplary biologically active moieties may comprise, e.g., an antigen binding fragment of an antibody molecule or portion thereof (e.g., F(ab), scFv, a VH domain, or a VL domain) (e.g., to act as a targeting moiety or to impart, induce or block a biological response), a ligand binding portion of a receptor or a receptor binding portion of a ligand, and Fc domain or moiety thereof, a complete Fc region, an scFc domain, an enzyme, etc. In one embodiment, a biologically active moiety comprises the mature form of a protein. In another embodiment, a biologically active moiety comprises a portion of a full length protein which retains biological activity.

In addition, as used herein, the term "biologically active moiety" includes, for example, moieties which may not have activity when present alone in monomeric form, but which have a biological activity when paired with a second moiety in the context of a dimeric molecule.

In one embodiment, a polypeptide of the invention which comprises a linker peptide is a "chimeric" or "fusion" protein. Such proteins comprises a first amino acid sequence linked to a second amino acid sequence to which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric polypeptides include fusion proteins comprising the linking peptides of the invention.

Polypeptides which comprise a linking peptide of the invention may be either monomeric or multimeric. For example, in one embodiment, a protein of the invention is a dimer. In one embodiment, the dimers of the invention are homodimers, comprising two identical monomeric subunits or polypeptides. In another embodiment, a dimeric polypeptide of the invention is a heterodimer, comprising two non-identical monomeric subunits or polypeptides (e.g., comprising two different biologically active moieties or one biologically active moiety only).

In one embodiment, a polypeptide of the invention is a binding molecule, i.e., a polypeptide that comprises a binding domain or binding site. The terms "binding domain" or "binding site", as used herein, refer to the portion, region, or site of polypeptide that mediates specific binding with a target molecule (e.g. an antigen, ligand, receptor, substrate or inhibitor). Exemplary binding domains include an antigen binding site (e.g., a VH and/or VL domain) or molecules comprising such a binding site (e.g., an antibody), a receptor binding domain of a ligand, a ligand binding domain of a receptor or a catalytic domain. The term "ligand binding domain" as used herein refers to a native receptor (e.g., cell surface receptor) or a region or derivative thereof retaining at least a qualitative ligand binding ability, and preferably the biological activity of the corresponding native receptor. The term "receptor binding domain" as used herein refers to a native ligand or region or derivative thereof retaining at least a qualitative receptor binding ability, and preferably the biological activity of the corresponding native ligand. In one embodiment, the polypeptides of the invention have at least one binding domain specific for a molecule targeted for reduction or elimination, e.g., a cell surface antigen or a soluble antigen. In one embodiment, the binding domain comprises or consists of an antigen binding site (e.g., comprising a variable heavy chain sequence and variable light chain sequence or six CDRs from an antibody placed into alternative framework regions (e.g., human framework regions optionally comprising one or more amino acid substitutions). In one embodiment, a binding domain serves as a targeting moiety.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen).

In one embodiment, a biologically active moiety comprises an Fc region, or domain or moiety thereof. As used herein, the term "Fc region" shall be defined as the portion of a polypeptide which corresponds to the Fc region of native immunoglobulin, i.e., as formed by the dimeric association of the respective Fc domains (or Fc moieties) of its two heavy chains. A native Fc region is homodimeric and comprises two polypeptide chains. In contrast, the term "genetically-fused Fc region" or "single-chain Fc region" (scFc region), as used herein, refers to a synthetic dimeric Fc region comprised of Fc domains (or Fc moieties) genetically linked within a single polypeptide chain (i.e., encoded in a single contiguous genetic sequence).

In certain aspects, the invention provides binding polypeptides comprising at least one genetically fused Fc region or portion thereof within a single polypeptide chain (i.e., binding polypeptides comprising a single-chain Fc (scFc) region). Preferred polypeptides of the invention comprise at least two Fc moieties (e.g., 2, 3, 4, 5, 6, or more Fc moieties) or Fc moieties within the same linear polypeptide chain. Preferably, at least two (more preferably all) of the Fc moieties are capable of folding (e.g., intramolecularly or intermolecularly folding) to form at least one functional scFc region which imparts an effector function to the polypeptide. For example, in one preferred embodiment, a binding polypeptide of the invention is capable of binding, via its scFc region, to an Fc receptor (e.g. an FcRn, an FcγR receptor (e.g., FcγRIII), or a complement protein (e.g. C1q)) in order to trigger an immune effector function (e.g., antibody-dependent cytotoxicity (ADCC), phagocytosis, or complement-dependent cytotoxicity (CDCC)).

In certain embodiments, at least two of the Fc moieties of the genetically fused Fc region (i.e., scFc region) are directly fused to each other in a contiguous linear sequence of amino acids such that there is no intervening amino acid or peptide between the C-terminus of the first Fc moiety and the N-terminus of the second Fc moiety. In more preferred embodiments, however, at least two of the Fc moieties (more preferably all) present in the genetically-fused Fc region (i.e., scFc region) are genetically fused via a linker peptide of the invention which is interposed between the at least two Fc moieties. The polypeptide linker ensures optimal folding, alignment, and/or juxtaposition of the at least two Fc moieties such that the scFc region is capable of binding with suitable affinity to an Fc receptor, thereby triggering an effector function. In certain embodiments, the genetically-fused Fc region (i.e., scFc region) is capable of binding to an Fc receptor with a binding affinity of at least $10^{-7}$ M (e.g., at least $10^{-8}$ M, at least $10^{-9}$ M, at least $10^{40}$ M, at least $10^{-11}$ M, or at least $10^{-12}$ M).

In certain embodiments, the polypeptides of the invention may comprise a scFc region comprising Fc moieties of the same, or substantially the same, sequence composition (herein termed a "homomeric scFc region"). In other embodiments, the polypeptides of the invention may comprise a scFc region comprising at least two Fc moieties which are of different sequence composition (i.e., herein termed a "heteromeric scFc region"). In certain embodiments, the binding polypeptides of the invention comprise a scFc region comprising at least one insertion or amino acid substitution. In one exemplary embodiment, the heteromeric scFc region comprises an amino acid substitution in a first Fc moiety (e.g., an amino acid substitution of Asparagine at EU position 297), but not in a second Fc moiety.

In certain embodiments, the scFc region is hemi-glycosylated. For example, the heteromeric scFc region may comprise a first, glycosylated, Fc moiety (e.g., a glycosylated CH2 region) and a second, aglycosylated, Fc moiety (e.g., an aglycosylated CH2 region), wherein a linker is interposed between the glycosylated and aglycosylated Fc moieties. In other embodiments, the scFc region is fully glycosylated, i.e., all of the Fc moieties are glycosylated. In still further embodiments, the scFc region may be aglycosylated, i.e., none of the Fc moieties are glycosylated.

As used herein, the term "Fc domain" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain. As used herein, the term "Fc region" refers to dimerized Fc domains which resemble the Fc region of native antibodies (e.g., whether made in the traditional two polypeptide chain format or as a single chain Fc region).

As used herein, the term "Fc domain portion" or "Fc moiety" includes an amino acid sequence of an Fc domain or derived from an Fc domain. In certain embodiments, an Fc moiety comprises at least one of: a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

In one embodiment, an Fc moiety of the invention comprises at least the portion of an Fc molecule known in the art to be required for FcRn binding, referred to herein as a neonatal receptor (FcRn) binding partner. An FcRn binding partner is a molecule or portion thereof that can be specifically bound by the FcRn receptor with consequent active transport by the FcRn receptor of the FcRn binding partner. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than 106 M-1, or more preferably higher than 108 M-1. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners of the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. As an example, one specific embodiment, incorporates the N297A mutation, removing a highly conserved N-glycosylation site. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Moreover, one of the FcRn binding partners of a construct of the invention may be mutated and the other FcRn binding partner not mutated at all, or they both may be mutated but with different mutations.

Certain of the above mutations may confer new functionality upon the FcRn binding partner. For example, one embodiment incorporates N297A, removing a highly conserved N-glycosylation site. The effect of this mutation is to reduce immunogenicity, thereby enhancing circulating half life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591).

In one embodiment, the FcRn binding partner is a polypeptide including the sequence PKNSSMISNTP (SEQ ID NO:14) and optionally further including a sequence selected from HQSLGTQ (SEQ ID NO:15), HQNLSDGK (SEQ ID NO:16), HQNISDGK (SEQ ID NO:17), or VISSHLGQ (SEQ ID NO:18) (U.S. Pat. No. 5,739,277).

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

The skilled artisan will understand that portions of an immunoglobulin constant region for use in a polypeptide of the invention can include mutants or analogs thereof, or can include chemically modified immunoglobulin constant regions (e.g. pegylated), or fragments thereof (see, e.g., Aslam and Dent 1998, Bioconjugation: Protein Coupling Techniques For the Biomedical Sciences Macmilan Reference, London). In one instance, a mutant can provide for enhanced binding of an FcRn binding partner for the FcRn.

Also contemplated for use in the chimeric protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display or via chemical library screening (see, e.g., McCafferty et al. 1990, Nature 348:552, Kang et al. 1991, Proc. Natl. Acad. Sci. USA 88:4363; EP 0 589 877 B1).

In another embodiment, an Fc region of the invention (e.g., an scFc region) comprises at least the portion of an Fc molecule known in the art to be required for FcγR binding.

In one embodiment, an Fc region of the invention (e.g., an scFc region) comprises at least the portion of an Fc molecule known in the art to be required for Protein A binding. In one embodiment, an Fc region of the invention (e.g., an scFc region) comprises at least the portion of an Fc molecule known in the art to be required for protein G binding.

As set forth herein, it will be understood by one of ordinary skill in the art that an Fc domain may also be modified by including one or more amino acid changes (substitutions, additions or deletions) such that it varies in amino acid sequence from a wild type Fc moiety. Many such changes or alterations are known in the art. In certain exemplary embodiments, the Fc moiety retains an effector function (e.g., FcγR binding) and in certain embodiments, the Fc moiety lacks or has reduced effector function.

The Fc domains or moieties of a polypeptide of the invention may be from any isotype (A, E, G, D or M) and may be derived from different immunoglobulin molecules. For example, an Fc domain or moiety of a polypeptide may comprise a CH2 and/or CH3 domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

In one embodiment, a linker peptide connects or genetically fuses one or more Fc moieties to a non-Fc polypeptide, e.g., a binding domain.

Polypeptides comprising the linker peptides of the invention can be made using techniques that are known in the art. In one embodiment, the polypeptides of the invention are "recombinant produced," i.e., are produced using recombinant DNA technology. Exemplary techniques for making the polypeptides of the invention are set forth in more detail below.

II. Linker Peptides

The polypeptides of the invention comprise at least one linker peptide. In one embodiment, a polypeptide comprises between 1 and 30 linker peptides, inclusive. In one embodiment, two or more linker peptides are present in a polypeptide of the polypeptide of the invention. In another embodiment, a polypeptide of the invention comprises 3, 4, 5, 6, 7, 8, 9 or 10 linker peptides.

Linker peptides of the invention may occur one time at a given position, or may occur multiple times (i.e., the sequence of the linker peptide may be repeated x times in sequence) at a given position in a recombinant polypeptide. For example, in one embodiment, a linker peptide of the invention is repeated between 1 and 10 times (inclusive) at a given position in a polypeptide. In another embodiment, a linker peptide occurs 2, 3, 4, 5, 6, 7, 8, 9 or 10 times at a given position in a polypeptide.

The linker peptides of the invention are modified from those in the art such that the amino acid sequence GSG (that occurs at the junction of traditional Gly/Ser linker peptide repeats) is not present. While not wishing to be bound by theory, the GSG sequence in traditional linker peptides may be acting as a weak consensus for the Gorge resident xylosyltransferase I and/or II. The linker peptides of the invention, therefore, comprise an amino acid sequence selected from the group consisting of: $(GGGXX)_n GGGGS$ and $GGGGS(XGGGS)_n$, where X is any amino acid that can be inserted into the sequence and not result in a polypeptide comprising the sequence GSG.

In one embodiment, the sequence of a linker peptide is $(GGGX_1X2)_n GGGGS$ and $X_1$ is P and $X_2$ is S. In one embodiment, the sequence of a linker peptide is $(GGGX_1X_2)_n GGGGS$ and $X_1$ is G and $X_2$ is Q. In one embodiment, the sequence of a linker peptide is $(GGGX_1X_2)_n GGGGS$ and $X_1$ is G and $X_2$ is A. In another embodiment, the sequence of a linker peptide is $GGGGS(XGGGS)_n$, and X is P.

In one embodiment, a linker peptide of the invention comprises or consists of the amino acid sequence $(GGGXX)_2 GGGGS$. In another embodiment, a linker peptide comprises or consists of the amino acid sequence $GGGGS(XGGGS)_2$.

In one embodiment, a linker peptide of the invention comprises or consists of the amino acid sequence $(GGGGA)_2 GGGGS$. In another embodiment, a linker peptide comprises or consists of the amino acid sequence $(GGGGQ)_2 GGGGS$. In another embodiment, a linker peptide comprises or consists of the amino acid sequence $(GGGPS)_2 GGGGS$. In another embodiment, a linker peptide comprises or consists of the amino acid sequence $GGGGS(PGGGS)_2$.

Linker peptides of the invention can be of varying lengths. In one embodiment, a linker peptide of the invention is from about 5 to about 75 amino acids in length. In another embodiment, a linker peptide of the invention is from about 5 to about 50 amino acids in length. In another embodiment, a linker peptide of the invention is from about 10 to about 40 amino acids in length. In another embodiment, a 15 linker peptide of the invention is from about 15 to about 35 amino acids in length. In another embodiment, a linker peptide of the invention is from about 15 to about 20 amino acids in length. In another embodiment, a linker peptide of the invention is from about 15 amino acids in length.

III. Exemplary Formats of Polypeptides Comprising Linker Peptides of the Invention The position(s) of a linker peptide(s) of the invention may vary depending on the nature of the polypeptide to be produced. Although many specific examples of polypeptides comprising linker peptides are disclosed herein, it will be understood that linker peptides may be positioned at least wherever linker peptides are presently positioned in recombinant polypeptides. Linker peptides are so frequently used in protein engineering that they have become standard assembly parts in synthetic biology (see e.g., Anderson, J. C., et al. Journal of Biological Engineering 2010. 4:1 and the partsregistry.org web site which lists standard biological parts used in genetic constructs).

Some examples of current, art recognized uses for linker peptides include uses in: scFv molecules (Freund et al. FEBS 1993. 320:97); single chain immunoglobulin molecules (Shun et al. 1993. PNAS. USA 90:7995); minibodies (Hun et al. 1996 Cancer Res. 56:3055); CH2 domain deleted antibodies (Mueller, B. M., et al. 1990 PNAS USA. 87:5702); single chain bispecific antibodies (Schertz et al. 2005 Cancer Res. 65:2882); full-length IgG-like bispecific antibodies (Marvin, J. S. et al. 2005 Act Pharmacology Sin 26:649 and the references cited therein as well as Michelson, J. S., et al. 2009 MAbs. 1:128 and Routt K. D. et al. 2010 Protein Eng Des Sell. 23:221); scFv fusion proteins (degree et al. 2002 British Journal of Cancer 86:811); developing protein-fragment complementation assays (Remy, I. et al. 2007 BioTechiques 42: 137), and in scFc molecules (e.g., as described in Exemplary scFc regions are disclosed in PCT Application No. PCT/US2008/006260, filed May 14, 2008, which is incorporated by reference herein).

Linker peptides may be attached to the N or to the C terminus (or both) of polypeptides to which they are attached.

In another embodiment, a linker peptide of the invention can be used to genetically fuse two biologically active moieties. In one embodiment, a linker peptide of the invention is used to fuse two moieties to each other, wherein neither moiety has biological activity alone, but when genetically fused, is biologically active. For example, in one embodiment, a linker peptide of the invention can be used to genetically fuse the VH and VL variable domains in an scFv molecule:

A-L-B, wherein A is VH or VL, B is VH or VL, and L is a linker peptide or A-L-B-L, wherein A is VH or VL, B is VH or VL, and L is a linker peptide In another embodiment, a linker peptide can be used to genetically fuse a biologically active moiety to a complete Fc region, an Fc domain, an Fc moiety, or an scFc region:

C-L-Fc, wherein C is a biologically active moiety, L is a linker peptide, and Fc is an Fc region (e.g., single chain or traditional two polypeptide chain), Fc domain, an Fc moiety, or an scFc region.

For example, in one embodiment, C comprises a scFv molecule (e.g., comprising VH-L-VL or VL-L-VH, where L is a linker peptide) and Fc consists of a Fc region (hinge-CH2-CH3 domain) or an scFc region, thus forming a scFv-Fc fusion protein or a scFv-scFc fusion protein.

In another embodiment, C comprises an scFv molecule (e.g., comprising VH-L-VL or VL-L-VH, where L is a linker peptide) and Fc is a CH3 domain, thus forming a minibody. In another embodiment, C comprises two tandem scFv molecules and an Fc moiety which is a CH3 domain, thereby forming a tetravalent minibody. A tetravalent minibody may also be formed using the format:

A-L-B-L-Fc-L-A-L-B, where A and B are each one of a VH or VL domain, L is a linker peptide and Fc is a CH3 domain or an scFc region.

In another embodiment, a polypeptide of the invention may have the format:

D-L-A-L-B, where D is a complete antibody molecule, L is a linker peptide, and A and B are each a VH or VL domain. Such a construct yields a C-terminal tetravalent antibody molecule.

In another embodiment, a polypeptide of the invention may have the format:

A-L-B-L-D, where D is a complete antibody molecule, L is a linker peptide, and A and B are each a VH or VL domain. Such a construct yields an N-terminal tetravalent antibody molecule. In such a construct, the A-L-B (scFv) portion of the molecule may be genetically fused to either the light chain or the heavy chain variable region.

In another embodiment, a linker peptide of the invention can be used to fuse a CH3 domain (or synthetic CH3 domain) to a hinge region (or synthetic hinge region). In another embodiment, a linker peptide of the invention can be used to fuse a CH3 domain (or synthetic CH3 domain) to a CH1 domain (or synthetic CH1 domain). In still another embodiment, a linker peptide can act as a peptide spacer between the hinge region (or synthetic hinge region) and a CH2 domain (or a synthetic CH2 domain). Preferred locations for linkers are between the Fc and the scFv of a binding molecule and/or between the VH and VL domains of an scFv molecule.

Where more than one binding site is included in a polypeptide, it will be understood that such molecules may be monospecific or multispecific, i.e., the binding sites may be the same or may be different.

Connecting peptides can be introduced into polypeptide sequences using techniques known in the art. Modifications can be confirmed by DNA sequence analysis. Plasmid DNA can be used to transform host cells for stable production of the polypeptides produced.

IV. Exemplary Biologically Active Moieties

The polypeptides of the invention comprise at least one biologically active moiety. Such a moiety can be biologically active as a single chain or may require association with another polypeptide chain (e.g., when linked with a second polypeptide via a linker peptide or when present in a polypeptide dimer).

In one embodiment, the polypeptides of the invention comprise only one biologically active moiety (creating a molecule which is monomeric with regard to the biologically active moiety, but which may be monomeric or dimeric with regard to the number of polypeptide chains). In another embodiment, a polypeptide of the invention comprises more than one biologically active moiety, e.g., 2, 3, 4, 5, 6, 7, 8, 9, 10, or more biologically active moieties. As used herein, the term "biologically active moiety" is not meant to include chemical effector moieties that may be added to a polypeptide (e.g., toxic moieties, detectable moieties and the like).

In one embodiment of the invention, a biologically active moiety is operably linked via a linker peptide to the N-terminus of an Fc domain, region, or moiety. In another embodiment, the biologically active moiety is operably linked via a linker peptide to the C-terminus of an Fc domain, region, or moiety.

In other embodiments, two or more biologically active moieties are linked to each other (e.g., via a linker peptide) in series. In one embodiment, the tandem array of biologically active moieties is operably linked via a linker peptide to either the C-terminus or the N-terminus of an Fc region, domain, or moiety.

In one embodiment, a polypeptide of the invention comprises at least one of an antigen binding site (e.g., an antigen binding site of an antibody, antibody variant, or antibody fragment), a receptor binding portion of ligand, or a ligand binding portion of a receptor.

In one embodiment, a biologically active moiety comprises an antigen binding site. In certain embodiments, the polypeptides of the invention have at least one binding site specific for a target molecule which mediates a biological effect. In one embodiment, the binding site modulates cellular activation or inhibition (e.g., by binding to a cell surface receptor and resulting in transmission of an activating or inhibitory signal). In one embodiment, the binding site is capable of initiating transduction of a signal which results in death of the cell (e.g., by a cell signal induced pathway, by complement fixation or exposure to a payload (e.g., a toxic payload) present on the binding molecule), or which modulates a disease or disorder in a subject (e.g., by mediating or promoting cell killing, by promoting lysis of a fibrin clot or promoting clot formation, or by modulating the amount of a substance which is bioavailable (e.g., by enhancing or reducing the amount of a ligand such as TNF in the subject)). In another embodiment, the polypeptides of the invention have at least one binding site specific for an antigen targeted for reduction or elimination, e.g., a cell surface antigen or a soluble antigen).

In another embodiment, binding of the polypeptides of the invention to a target molecule (e.g. antigen) results in the reduction or elimination of the target molecule, e.g., from a tissue or from circulation. In another embodiment, a polypeptide has at least one binding site specific for a target molecule and can be used to detect the presence of the target molecule (e.g., to detect a contaminant or diagnose a condition or disorder). In yet another embodiment, a polypeptide of the invention comprises at least one binding site that targets the molecule to a specific site in a subject (e.g., to a tumor cell, an immune cell, or blood clot).

In certain embodiments, the polypeptides of the invention may comprise two or more biologically active moieties. In one embodiment, the biologically active moieties are identical. In another embodiment, the biologically active moieties are different.

In certain particular aspects, a binding polypeptide of the invention is multispecific, e.g., has at least one binding site that binds to a first molecule or epitope of a molecule and at least one second binding site that binds to a second molecule or to a second epitope of the first molecule. Multispecific binding molecules of the invention may comprise at least two binding sites. In certain embodiments, at least one binding site of a multispecific binding molecule of the invention is an antigen binding region of an antibody or an antigen binding fragment thereof (e.g. an antibody or antigen binding fragment).

Exemplary biologically active moieties are discussed further below:

i. Antigen Binding Portions

In certain embodiments, a polypeptide of the invention comprises at least one antigen binding portion (binding site) of an antibody. In one embodiment, the antigen binding portion targets the composition to a particular cell type or tissue.

In other embodiments, a binding site of a polypeptide of the invention may comprise an antigen binding fragment. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, said antigen binding fragments can be derived from any of the antibodies or antibody variants described supra. Antigen binding portions can be produced by recombinant or biochemical methods that are well known in the art. Exemplary antigen-binding fragments include VH or VL (if either variable region alone is sufficient to bind antigen), Fv, Fab, Fab', and (Fab')$_2$.

In other embodiments, a binding molecule of the invention may comprise a binding site from single chain binding molecule (e.g., a single chain variable region or scFv). Techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain binding molecules. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242: 1038-1041 (1988)).

In certain embodiments, a polypeptide of the invention comprises one or more binding sites or regions comprising or consisting of a single chain variable region sequence (scFv). Single chain variable region sequences comprise a single polypeptide having one or more antigen binding sites, e.g., a $V_L$ domain linked by a linker peptide to a $V_H$ domain. The VL and/or VH domains may be derived from antibodies known in the art or variants thereof. ScFv molecules can be constructed in a $V_H$-linker-$V_L$ orientation or $V_L$-linker-$V_H$ orientation.

In certain embodiments, a scFv molecule employed in a polypeptide of the invention is a stabilized scFv molecule. In one embodiment, the stabilized scFv molecule may comprise a linker peptide interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which it is operably linked. Exemplary stabilized scFv molecules which may be present in the polypeptides of the invention are described in U.S. Provisional Patent Application No. 60/873,996, filed on Dec. 8, 2006 or U.S. patent application Ser. No. 11/725,970, filed on Mar. 19, 2007, each of which is incorporated herein by reference in its entirety.

In certain exemplary embodiments, the polypeptides of the invention comprise at least one scFv molecule that is operably linked via a linker peptide to the C-terminus and/or N-terminus of an Fc region.

Polypeptides of the invention may comprise a variable region or portion thereof (e.g. a VL and/or VH domain) derived from an antibody using art recognized protocols. For example, the variable domain may be derived from antibody produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

While the variable region may be derived from polyclonal antibodies harvested from the serum of an immunized mammal, it is often desirable to isolate individual lymphocytes from the spleen, lymph nodes or peripheral blood to provide homogenous preparations of monoclonal antibodies (MAbs) from which the desired variable region is derived. Rabbits or guinea pigs are typically used for making polyclonal antibodies. Mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well known process (Kohler et al., (1975), *Nature,* 256:495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the antibody genetically encoded by the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunosorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice,* pp 59-103 (Academic Press, 1986)). It will further be appreciated that the monoclonal antibodies secreted by the subclones may be separated from culture medium, ascites fluid or serum by conventional purification procedures such as, for example, affinity chromatography (e.g., protein-A, protein-G, or protein-L affinity chromatography), hydroxylapatite chromatography, gel electrophoresis, or dialysis.

Optionally, antibodies may be screened for binding to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

DNA encoding the desired monoclonal antibody may be readily isolated and sequenced using any of the conventional procedures described supra for the isolation of constant region domain sequences (e.g., by using oligonucleotide probes that are capable of binding specifically to genes encoding the heavy and light chains of murine antibodies). The isolated and subcloned hybridoma cells serve as a preferred source of such DNA. More particularly, the isolated DNA (which may be synthetic as described herein) may be used to clone the desired variable region sequences for incorporation in the polypeptides of the invention.

In other embodiments, the binding site is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific antibodies that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, variable (V) domains can be obtained from libraries of variable gene sequences from an animal of choice. Libraries expressing random combinations of domains, e.g., $V_H$ and $V_L$ domains, can be screened with a desired antigen to identify elements which have desired binding characteristics. Methods of such screening are well known in the art. For example, antibody gene repertoires can be cloned into a λ bacteriophage expression vector (Huse, W D et al. (1989). *Science*, 2476: 1275). In addition, cells (Francisco et al. (1994), *PNAS*, 90:10444; Georgiou et al. (1997), *Nat. Biotech.*, 15:29; Boder and Wittrup (1997) *Nat. Biotechnol.* 15:553; Boder et al. (2000), *PNAS*, 97:10701; Daugtherty, P. et al. (2000) *J. Immunol. Methods.* 243:211) or viruses (e.g., Hoogenboom, H R. (1998), *Immunotechnology* 4:1; Winter et al. (1994). *Annu. Rev. Immunol.* 12:433; Griffiths, A D. (1998). *Curro Opin. Biotechnol.* 9: 102) expressing antibodies on their surface can be screened.

Those skilled in the art will also appreciate that DNA encoding antibody variable domains may also be derived from antibody libraries expressed in phage, yeast, or bacteria using methods known in the art. Exemplary methods are set forth, for example, in EP 368 684 B1; U.S. Pat. No. 5,969,108; Hoogenboom et al., (2000) *Immunol. Today* 21:371; Nagy et al. (2002) *Nat. Med.* 8:801; Huie et al. (2001), *PNAS*, 98:2682; Lui et al. (2002), *J. Mol. Bioi.* 315:1063, each of which is incorporated herein by reference. Several publications (e.g., Marks et al. (1992), *Bio/Technology* 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes, et al. (1998), *PNAS* 95:14130; Hanes and Pluckthun. (1999), *Curro Top. Microbiol. Immunol.* 243:107; He and Taussig. (1997), *Nuc. Acids Res.*, 25:5132; Hanes et al. (2000), *Nat. Biotechnol.* 18:1287; Wilson et al. (2001), *PNAS*, 98:3750; or Irving et al. (2001) *J. Immunol. Methods* 248:31).

Preferred libraries for screening are human variable gene libraries. VL and $V_H$ domains from a non-human source may also be used. Libraries can be naïve, from immunized subjects, or semi-synthetic (Hoogenboom and Winter. (1992). *J. Mol. Biol.* 227:381; Griffiths et al. (1995) *EMBO J.* 13:3245; de Kruif et al. (1995). *J. Mol. Biol.* 248:97; Barbas et al. (1992), *PNAS*, 89:4457). In one embodiment, mutations can be made to immunoglobulin domains to create a library of nucleic acid molecules having greater heterogeneity (Thompson et al. (1996), *J. Mol. Biol.* 256:77; Lamminmaki et al. (1999), *J. Mol. Biol.* 291:589; Caldwell and Joyce. (1992), *PCR Methods Appl.* 2:28; Caldwell and Joyce. (1994), *PCR Methods Appl.* 3:S136). Standard screening procedures can be used to select high affinity variants. In another embodiment, changes to $V_H$ and $V_L$ sequences can be made to increase antibody avidity, e.g., using information obtained from crystal structures using techniques known in the art.

Moreover, variable region sequences useful for producing the polypeptides of the present invention may be obtained from a number of different sources. For example, as discussed above, a variety of human gene sequences are available in the form of publicly accessible deposits. Many sequences of antibodies and antibody-encoding genes (e.g., antibodies known to have clinically beneficial properties) have been published and suitable variable region sequences (e.g. VL and VH sequences) can be chemically synthesized from these sequences using art recognized techniques.

In another embodiment, at least one variable region domain present in a polypeptide of the invention is catalytic (Shokat and Schultz. (1990). *Annu. Rev. Immunol.* 8:335). Variable region domains with catalytic binding specificities can be made using art recognized techniques (see, e.g., U.S. Pat. No. 6,590,080, U.S. Pat. No. 5,658,753). Catalytic binding specificities can work by a number of basic mechanisms similar to those identified for enzymes to stabilize the transition state, thereby reducing the free energy of activation. For example, general acid and base residues can be optimally positioned for participation in catalysis within catalytic active sites; covalent enzyme-substrate intermediates can be formed; catalytic antibodies can also be in proper orientation for reaction and increase the effective concentration of reactants by at least seven orders of magnitude (Fersht et al., (1968), *J. Am. Chem. Soc.* 90:5833) and thereby greatly reduce the entropy of a chemical reaction. Finally, catalytic antibodies can convert the energy obtained upon substrate binding and/or subsequent stabilization of the transition state intermediate to drive the reaction.

Acid or base residues can be brought into the antigen binding site by using a complementary charged molecule as an immunogen. This technique has proved successful for elicitation of antibodies with a hapten containing a positively-charged ammonium ion (Shokat, et al., (1988), *Chem. Int. Ed. Engl.* 27:269-271). In another approach, antibodies can be elicited to stable compounds that resemble the size, shape, and charge of the transition state intermediate of a desired reaction (i.e., transition state analogs). See U.S. Pat. No. 4,792,446 and U.S. Pat. No. 4,963,355 which describe the use of transition state analogs to immunize animals and the production of catalytic antibodies. Both of these patents are hereby incorporated by reference. Such molecules can be administered as part of an immunoconjugate, e.g., with an immunogenic carrier molecule, such as KLH.

In another embodiment, a binding domain of a polypeptide of the invention consists of a $V_H$ domain, e.g., derived from camelids, which is stable in the absence of a $V_L$ chain (Hamers-Casterman et al. (1993). *Nature,* 363:446; Desmyter et al. (1996). *Nat. Struct. Biol.* 3: 803; Decanniere et al. (1999). *Structure*, 7:361; Davies et al. (1996). *Protein Eng.,* 9:531; Kortt et al. (1995). *J. Protein Chem.*, 14:167).

A polypeptide of the invention may comprise a variable domain or CDR(s) derived from a fully murine, fully human, chimeric, humanized, non-human primate or primatized antibody. Non-human antibodies, or fragments or domains thereof, can be altered to reduce their immunogenicity using art recognized techniques. Humanized antibodies are antibodies derived from non-human antibodies, that have been modified to retain or substantially retain the binding properties of the parent antibody, but which are less immunogenic in humans that the parent, non-human antibodies. In the case of humanized target antibodies, this may be achieved by various methods, including (a) grafting the entire non-human variable domains onto human constant regions to generate chimeric target antibodies; (b) grafting at least a part of one or more of the non-human complementarity determining regions (CDRs) into a human framework and constant regions with or without retention of critical framework residues; (c) transplanting the entire non-human variable domains, but "cloaking" them with a human-like section by replacement of surface residues. Such methods are disclosed in Morrison et al., (1984), *PNAS.* 81: 6851-5; Morrison et al., (1988), *Adv. Immunol.* 44: 65-92; Verhoeyen et al., (1988), *Science* 239: 1534-1536; Padlan, (1991), *Molec. Immun.* 28: 489-498; Padlan, (1994), *Molec. Immun.* 31: 169-217; and U.S. Pat. Nos. 5,585,089, 5,693,761 and 5,693,762 all of which are hereby incorporated by reference in their entirety.

De-immunization can also be used to decrease the immunogenicity of a polypeptide of the invention. As used herein, the term "de-immunization" includes modification of T cell epitopes (see, e.g., WO9852976A1, WO0034317A2). For example, VH and VL sequences are analyzed and a human T cell epitope "map" from each V region showing the location of epitopes in relation to complementarity-determining regions (CDRs) and other key residues within the sequence is generated. Individual T cell epitopes from the T cell epitope map are analyzed in order to identify alternative amino acid substitutions with a low risk of altering the activity of the final antibody. A range of alternative VB and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

In one embodiment, the variable domains employed in a polypeptide of the invention are altered by at least partial replacement of one or more CDRs. In another embodiment, variable domains can optionally be altered, e.g., by partial framework region replacement and sequence changing. In making a humanized variable region the CDRs may be derived from an antibody of the same class or even subclass as the antibody from which the framework regions are derived, however, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the binding domain. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antigen binding site with reduced immunogenicity.

In one embodiment, a polypeptide of the invention comprises at least one CDR from an antibody that recognizes a desired target. In another embodiment, an altered antibody of the present invention comprises at least two CDRs from an antibody that recognizes a desired target. In another embodiment, an altered antibody of the present invention comprises at least three CDRs from an antibody that recognizes a desired target. In another embodiment, an altered antibody of the present invention comprises at least four CDRs from an antibody that recognizes a desired target. In another embodiment, an altered antibody of the present invention comprises at least five CDRs from an antibody that recognizes a desired target. In another embodiment, an altered antibody of the present invention comprises all six CDRs from an antibody that recognizes a desired target. In one embodiment, a polypeptide of the invention comprises the complete amino acid sequence of an antibody molecule that recognizes a desired target (e.g., in the case of a bispecific, tetravalent antibody molecule).

Exemplary antibodies from which binding sites can be derived for use in the binding molecules of the invention are known in the art. For example, antibodies currently approved by the FDA for use in treatment can be used to derive binding sites.

In one embodiment, a polypeptide of the invention binds to a molecule which is associated with cancer cells and the polypeptide is useful in treating cancer.

In still other embodiments, a polypeptide of the invention binds to a molecule which is useful in treating an autoimmune or inflammatory disease or disorder.

For example, a polypeptide may bind to an antigen present on an immune cell (e.g., a B or T cell) or an autoantigen responsible for an autoimmune disease or disorder. The antigen associated with an autoimmune or inflammatory disorder may be a tumor-associated antigen described supra. Thus, a tumor associated antigen may also be an autoimmune or inflammatory associated disorder. As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; Goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjogren's syndrome; ankylosing spondylitis; vasculitis; type I diabetes mellitus; neurological disorders, multiple sclerosis, and secondary diseases caused as a result of autoimmune diseases.

In other embodiments, the polypeptides of the invention bind to a target molecule associated with an inflammatory disease or disorder. As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). For example, a polypeptide of the invention may bind to an inflammatory factor (e.g., a matrix metalloproteinase (MMP), TNF, an interleukin, a plasma protein, a cytokine, a lipid metabolite, a protease, a toxic radical, a mitochondrial protein, an apoptotic protein, an adhesion molecule, etc.) involved or present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, e.g., lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories. Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

In yet other embodiments, a polypeptide of the invention binds to a molecule which is useful in treating a neurological disease or disorder. For example, a polypeptide may bind to an antigen present on a neural cell (e.g., a neuron, a glial cell, or a). In certain embodiments, the antigen associated with a neurological disorder may be an autoimmune or inflammatory disorder described supra. As used herein, the term "neurological disease or disorder" includes disorders or conditions in a subject wherein the nervous system either degenerates (e.g., neurodegenerative disorders, as well as disorders where the nervous system fails to develop properly or fails to regenerate following injury, e.g., spinal cord injury. Examples of neurological disorders that can be diagnosed, prevented or treated by the methods and compositions of the present invention include, but are not limited to, Multiple Sclerosis, Huntington's Disease, Alzheimer's Disease, Parkinson's Disease, neuropathic pain, traumatic brain injury, Guillain-Barré syndrome and chronic inflammatory demyelinating polyneuropathy (CIDP).

In one embodiment, a polypeptide of the invention is a molecule as described, e.g. in PCT/US2011/033752 (incorporated by reference herein) which includes, e.g. at least one extracellular domain of a human LIGHT protein or fragment thereof or an antibody that binds to LIGHT and which further includes a peptide linker of the invention.

In other aspects, the polypeptides of the invention may comprise a modified antibody molecule or an antigen binding site (or portions thereof) derived from a modified form of antibody. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other modified antibodies are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. 5 Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, a binding polypeptide of the invention comprises an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, an immature polypeptide of the invention comprises a diabody which is operably linked to the N-terminus and/or C-terminus of at least one genetically-fused Fc region (i.e., scFc region).

In certain embodiments, a polypeptide of the invention comprises a single domain binding molecule (e.g. a single domain antibody). Exemplary single domain molecules include an isolated heavy chain variable domain ($V_H$) of an antibody, i.e., a heavy chain variable domain, without a light chain variable domain, and an isolated light chain variable domain ($V_L$) of an antibody, i.e., a light chain variable domain, without a heavy chain variable domain. Exemplary single-domain antibodies employed in the binding molecules of the invention include, for example, the Camelid heavy chain variable domain (about 118 to 136 amino acid residues) as described in Hamers-Casterman, et al., Nature 363:446-448 (1993), and Dumoulin, et al., Protein Science 11:500-515 (2002). Other exemplary single domain antibodies include single VH or VL domains, also known as Dabs® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH. Methods for making single domain binding molecules are described in U.S. Pat. Nos. 6,005,079 and 6,765,087, both of which are incorporated herein by reference. Exemplary single domain antibodies comprising VHH domains include Nanobodies® (Ablynx NV, Ghent, Belgium).

ii. Non-Immunoglobulin Binding Molecules

In certain other embodiments, the polypeptides of the invention comprise one or more binding sites derived from a non-immunoglobulin binding molecule. As used herein, the term "non-immunoglobulin binding molecules" are binding molecules whose binding sites comprise an amino acid sequence derived from a polypeptide other than an immunoglobulin. Examples of binding molecules comprising binding sites not derived from antibody molecules include receptor binding sites and ligand binding sites which are discussed in more detail infra.

Non-immunoglobulin binding molecules can comprise binding site portions that are derived from a member of the immunoglobulin superfamily that is not an immunoglobulin (e.g. a T-cell receptor or a cell-adhesion protein (e.g., CTLA-4, N-CAM, telokin)). In other embodiments, non-immunoglobulin binding molecules of the invention also comprise a binding site with a protein topology that is not based on the immunoglobulin fold (e.g. such as ankyrin repeat proteins or fibronectins) but which nonetheless are capable of specifically binding to a target.

Non-immunoglobulin binding molecules may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified by their homology with the immunoglobulin fold. For example, residues within the CDR-like loops of fibronectin may be randomized to generate a library of fibronectin binding molecules (see, e.g., Koide et al., J. Mol. Biol., 284: 1141-1151 (1998)). Other portions of the binding site which may be randomized include flat surfaces. Selection can be achieved by art-recognized methods such as phage display, yeast display, or ribosome display.

In one embodiment, a polypeptide of the invention comprises a binding site from a fibronectin binding molecule. Fibronectin binding molecules (e.g., molecules comprising the Fibronectin type I, II, or III domains) display CDR-like loops which, in contrast to immunoglobulins, do not rely on intra-chain disulfide bonds. Methods for making fibronectin polypeptides are described, for example, in WO 01/64942 and in U.S. Pat. Nos. 6,673,901, 6,703,199, 7,078,490, and 7,119,171, which are incorporated herein by reference. In one exemplary embodiment, the fibronectin polypeptide is AdNectin® (Adnexus Therapeutics, Waltham, Mass.).

In another embodiment, a polypeptide of the invention comprises a binding site from an Affibody® (Abcam, Cambridge, Mass.). Affibodies are derived from the immunoglobulin binding domains of staphylococcal Protein A (SPA) (see e.g., Nord et al., Nat. Biotechnol., 15: 772-777 (1997)). Methods for making affibody binding sites are described in U.S. Pat. Nos. 6,740,734 and 6,602,977 and in WO 00/63243, each of which is incorporated herein by reference.

In another embodiment, a binding molecule of the invention comprises a binding site from an Anticalin® (Pieris A G, Friesing, Germany). Anticalins (also known as lipocalins) are members of a diverse B-barrel protein family whose function is to bind target molecules in their barrel/loop region. Lipocalin binding sites may be engineered by randomizing loop sequences connecting the strands of the barrel (see e.g., Schlehuber et al., Drug Discov. Today, 10: 23-33 (2005); Beste et al., PNAS, 96: 1898-1903 (1999). Anticalin binding sites employed in the binding molecules of the invention may be obtainable starting from polypeptides of the lipocalin family which are mutated in four segments that correspond to the sequence positions of the linear polypeptide sequence comprising amino acid positions 28 to 45, 58 to 69, 86 to 99 and 114 to 129 of the Bilin-binding protein (BBP) of *Pieris brassica*. Other methods for making anticalin binding sites are described in WO99/16873 and WO 05/019254, each of which is incorporated herein by reference.

In another embodiment, a polypeptide of the invention comprises a binding site from a cysteine-rich polypeptide. Cysteine-rich domains employed in the practice of the present invention typically do not form a α-helix, a β sheet, or a β-barrel structure. Typically, the disulfide bonds promote folding of the domain into a three-dimensional structure. Usually, cysteine-rich domains have at least two disulfide bonds, more typically at least three disulfide bonds. An exemplary cysteine-rich polypeptide is an A domain protein. A-domains (sometimes called "complement-type repeats") contain about 30-50 or 30-65 amino acids. In some embodiments, the domains comprise about 35-45 amino acids and in some cases about 40 amino acids. Within the 30-50 amino acids, there are about 6 cysteine residues. Of the six cysteines, disulfide bonds typically 15 are found between the following cysteines: C1 and C3, C2 and C5, C4 and C6. The A domain constitutes a ligand binding moiety. The cysteine residues of the domain are disulfide linked to form a compact, stable, functionally independent moiety. Clusters of these repeats make up a ligand binding domain, and differential clustering can impart specificity with respect to the ligand binding. Exemplary proteins containing A-domains include, e.g., complement components (e.g., C6, C7, C8, C9, and Factor I), serine proteases (e.g., enteropeptidase, matriptase, and corin), transmembrane proteins (e.g., ST7, LRP3, LRP5 and LRP6) and endocytic receptors (e.g., Sortilin-related receptor, LDL-receptor, VLDLR, LRP1, LRP2, and ApoER2). Methods for making A domain proteins of a desired binding specificity are disclosed, for example, in WO 02/088171 and WO 04/044011, each of which is incorporated herein by reference.

In other embodiments, a binding molecule of the invention comprises a binding site from a repeat protein. Repeat proteins are proteins that contain consecutive copies of small (e.g., about 20 to about 40 amino acid residues) structural units or repeats that stack together to form contiguous domains. Repeat proteins can be modified to suit a particular target binding site by adjusting the number of repeats in the protein. Exemplary repeat proteins include Designed Ankyrin Repeat Proteins (i.e., a DARPins®, Molecular Partners, Zurich, Switzerland) (see e.g., Binz et al., Nat. Biotechnol., 22:

575-582 (2004)) or leucine-rich repeat proteins (ie., LRRPs) (see e.g., Pancer et al., Nature, 430: 174-180 (2004)). All so far determined tertiary structures of ankyrin repeat units share a characteristic composed of a β-hairpin followed by two antiparallel α-helices and ending with a loop connecting the repeat unit with the next one. Domains built of ankyrin repeat units are formed by stacking the repeat units to an extended and curved structure. LRRP binding sites from part of the adaptive immune system of sea lampreys and other jawless fishes and resemble antibodies in that they are formed by recombination of a suite of leucine-rich repeat genes during lymphocyte maturation. Methods for making DARpin or LRRP binding sites are described in WO 02/20565 and WO 06/083275, each of which is incorporated herein by reference.

Other non-immunoglobulin binding sites which may be employed in binding molecules of the invention include binding sites derived from Src homology domains (e.g. SH2 or SH3 domains), PDZ domains, beta-lactamase, high affinity protease inhibitors, or small disulfide binding protein scaffolds such as scorpion toxins. Methods for making binding sites derived from these molecules have been disclosed in the art, see e.g., Silverman et al., Nat. Biotechnol., 23(12): 1493-4 (2005); Panni et al, J. Biol. Chem., 277: 21666-21674 (2002), Schneider et al., Nat. Biotechnol., 17: 170-175 (1999); Legendre et al., Protein Sci., 11:1506-1518 (2002); Stoop et al., Nat. Biotechnol., 21: 1063-1068 (2003); and Vita et al., PNAS, 92: 6404-6408 (1995). Yet other binding sites may be derived from a binding domain selected from the group consisting of an EGF-like domain, a Kringle-domain, a PAN domain, a G1a domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an Immunoglobulin-like domain, a C-type lectin domain, a MAM domain, a von Willebrand factor type A domain, a Somatomedin B domain, a WAP-type four disulfide core domain, a F5/8 type C domain, a Hemopexin domain, a Laminin-type EGF-like domain, a C2 domain, a CTLA-4 domain, and other such domains known to those of ordinary skill in the art, as well as derivatives and/or variants thereof. Additional non-immunoglobulin polypeptides include Avimers® (Avidia, Inc., Mountain View, Calif.—see International PCT Publication No. WO 06/055689 and US Patent Pub 2006/0234299), Telobodies® (Biotech Studio, Cambridge, Mass.), Evibodies® (Evogenix, Sydney, Australia—see U.S. Pat. No. 7,166,697), and Microbodies® (Nascacell Technologies, Munich, Germany).

iii. Binding Portions of Receptors or Ligands

In other aspects, a genetic construct of the invention comprises a nucleotide sequence encoding a ligand binding site of a receptor and/or a receptor binding portion of a ligand which is operably linked to at least one genetically-fused Fc region.

In certain embodiments, an immature polypeptide of the invention is a fusion of a ligand binding portion of a receptor and/or a receptor binding portion of a ligand with an Fc region. A transmembrane region or lipid or phospholipid anchor recognition sequences of the ligand binding receptor are preferably inactivated or deleted prior to fusion. DNA encoding the ligand or ligand binding partner is cleaved by a restriction enzyme at or proximal to the 5' and 3' ends of the DNA encoding the desired ORF segment. The resultant DNA fragment is then readily inserted (e.g., ligated in-frame) into DNA encoding a genetically-fused Fc region. The precise site at which the fusion is made may be selected empirically to optimize the secretion or binding characteristics of the soluble fusion protein. DNA encoding the fusion protein is then subcloned into an appropriate expression vector than can be transfected into a host cell for expression.

In one embodiment of a genetic construct of the invention, the binding domain of the ligand or receptor domain will be operably linked via a linker polypeptide to the C-terminus of a genetically-fused Fc region. N-terminal fusions are also possible. In exemplary embodiments, fusions are made to the C-terminus of the genetically-fused Fc region, or immediately N-terminal to the hinge domain a genetically-fused Fc region.

In other exemplary embodiments, a polypeptide of the invention may comprise one or more ligand binding domains or receptor binding domains derived from one or more of the following proteins or one or more antibodies binding to one or more of the following proteins:

a. Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, cytotoxic T lymphocyte antigen 4 (CTLA-4), and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IL10 receptor, IFNγ (EP0240975), and the TNF family of receptors (e.g., TNFα (e.g. TNFR-1 (EP 417, 563), TNFR-2 (EP 417,014) lymphotoxin beta receptor).

b. Adhesion Proteins

Adhesion molecules are membrane-bound proteins that allow cells to interact with one another. Various adhesion proteins, including leukocyte homing receptors and cellular adhesion molecules, or receptor binding portions thereof, can be incorporated in a fusion protein of the invention. Leukocyte homing receptors are expressed on leukocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

c. Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

d. Hormones

Exemplary growth hormones for use as biologically active moieties in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576, 608); follicle stimulating hormone (FSH); calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

e. Clotting Factors

Exemplary blood coagulation factors for use as biologically active moieties in the fusion proteins of the invention include the clotting factors (e.g., factors V, VII, VIII, IX, X, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

In one embodiment, more than one clotting factor may be present in a polypeptide of the invention.

f. Receptors and Ligands

In one embodiment, a polypeptide of the invention combines the binding site(s) of the ligand or receptor (e.g. the extracellular domain (ECD) of a receptor) with at least one genetically-fused Fc region (i.e., scFc region). In certain embodiments, the binding site or domain of the ligand-binding portion of a receptor may be derived from a receptor bound by an antibody or antibody variant. In other embodiments, the ligand binding portion of a receptor is derived from a receptor selected from the group consisting of a receptor of the Immunoglobulin (Ig) superfamily (e.g., a soluble T-cell receptor, e.g., mTCR® (Medigene A G, Munich, Germany), a receptor of the TNF receptor superfamily described supra (e.g., a soluble TNFα receptor of an immunoadhesin), a receptor of the Glial Cell-Derived Neurotrophic Factor (GDNF) receptor family (e.g., GFRα3), a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In other embodiments, the binding site or domain of the receptor-binding portion of a ligand may be derived from a ligand bound by an antibody or antibody variant. For example, the ligand may bind a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily. In one exemplary embodiment, the binding site of the receptor-binding portion of a ligand is derived from a ligand belonging to the TNF ligand superfamily (e.g., CD40L or LIGHT). In another exemplary embodiment, the antibody binds to a molecule in the TNF superfamily (e.g., CD40 or LTβR).

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), glial cell derived neurotrophic factor ligands (e.g., GDNF, neuturin, artemin, and persephin), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); Thrombopoeitin (TPO; stem-cell factor (SCF), thrombopoietin (TPO, c-Mpl ligand), and the Wnt polypeptides (U.S. Pat. No. 6,159,462).

Exemplary growth factor receptors which may be used as biologically active moieties of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as $p75^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)).

g. Heterodimeric Receptors

In one embodiment, antagonists to cytokines that utilize an a specificity determining component which, when combined with the cytokine, binds to a first β signal transducing component to form a nonfunctional intermediate which then binds to a second β signal transducing component causing β-receptor dimerization and consequent signal transduction can be made using the methods of the invention. Such molecules are described in the art (see e.g., U.S. Pat. No. 6,927,044). In one example, a soluble specificity determining component of the receptor and the extracellular domain of the first β signal transducing component of the cytokine receptor are combined to form a heterodimer that binds the cytokine to form a nonfunctional complex. Exemplary cytokines that can be inhibited using such heterodimeric receptors include: ILL IL-2, IL-3, IL-4, IL-5, IL-3, IL-4, IL-5, IL-11, IL-15, GMCSF, LIF, INPγ, and TGFβ.

V. Preparation of Polypeptides

Having selected the format of a polypeptide of the invention, a variety of methods are available for producing the polypeptide.

In one embodiment, the invention pertains to a nucleic acid construct comprising a nucleic acid sequence encoding a polypeptide molecule of the invention. It will be understood that because of the degeneracy of the code, a variety of nucleic acid sequences will encode the amino acid sequence of the polypeptide. The desired polynucleotide can be produced using methods known in the art (e.g., by de novo solid-phase DNA synthesis or by PCR mutagenesis of an earlier prepared polynucleotide encoding the target polypeptide).

Oligonucleotide-mediated mutagenesis is one method for preparing a substitution, in-frame insertion, or alteration (e.g., altered codon) to introduce a codon encoding an amino acid substitution (e.g., into an Fc variant moiety). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a polypeptide of the invention.

For recombinant production, a polynucleotide sequence encoding the polypeptide is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14:725) and electroporation (Neumann et al. 1982, EMBO, J. 1:841). A variety of host-expression vector systems may be utilized to express the polypeptide described herein in eukaryotic cells. In one embodiment, the eukaryotic cell is an animal cell, including mammalian cells (e.g. CHO, BHK, Cos, HeLa cells). When the polypeptide is expressed in a eukaryotic cell the DNA encoding the polypeptide may also code for a signal sequence that will permit the polypeptide to be secreted. One skilled in the art will understand that while the protein is translated the signal sequence is cleaved by the cell to form the mature polypeptide. In one embodiment, the invention pertains to mature polypeptides comprising a linker peptide of the invention. Alternatively, where a signal sequence is not included the polypeptide can be recovered by lysing the cells.

The polypeptide of the invention can also be synthesized in a transgenic animal, such as a rodent, goat, sheep, pig, or cow. The term "transgenic animals" refers to nonhuman animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82:4438). Methods of producing transgenic animals are known in the art, including transgenics that produce immunoglobulin molecules (Wagner et al. 1981, Proc. Natl. Acad. Sci. USA 78: 6376; McKnight et al. 1983, Cell 34:335; Brinster et al. 1983, Nature 306: 332; Ritchie et al. 1984, Nature 312: 517; Baldassarre et al. 2003, Theriogenology 59:831; Robl et al. 2003, Theriogenology 59: 107; Malas-sagne et al. 2003, Xenotransplantation 10 (3): 267).

Expression vectors can encode for tags that permit for easy purification or identification of the recombinantly produced polypeptide. Examples include, but are not limited to, vector pUR278 (Ruther et al. 1983, EMBO J. 2: 1791) in which the polypeptide described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g. PreCission Protease (Pharmacia, Peapack, N.J.)) for easy removal of the tag after purification.

For the purposes of this invention, numerous different art recognized expression vector systems may be employed.

These expression vectors are typically replicable in the host organisms either as episomes or as an integral part of the host chromosomal DNA. Expression vectors may include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors may also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

In other preferred embodiments the polypeptides of the instant invention may be expressed using polycistronic constructs. In these expression systems, multiple gene products of interest such as multiple polypeptides of multimer binding protein may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a polypeptide has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; *Bacillaceae*, such as *Bacillus subtilis*; *Pneumococcus*; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan. Other yeast hosts such *Pichia* may also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian large scale cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) may optionally be attached or included within the polypeptide sequence to facilitate downstream purification.

VI. Purification of Binding Molecules

Once expressed, polypeptides of the invention can be purified according to standard procedures in the art, including, e.g., ammonium sulfate precipitation, affinity column chromatography, HPLC purification, gel electrophoresis and the like (see generally Scopes, Protein Purification (Springer-Verlag, N.Y., (1982)). Substantially pure proteins of at least about 90 to 95% homogeneity are preferred, and 98 to 99% or more homogeneity most preferred, for pharmaceutical uses.

VII. Polypeptides Comprising Functional Moieties

The polypeptides of the present invention may be used in non-conjugated form or may be conjugated to at least one of a variety of functional effector moieties, e.g., to facilitate target detection or for imaging or therapy of the patient. The polypeptides of the invention can be labeled or conjugated either before or after purification, when purification is performed. In particular, the polypeptides of the present invention may be conjugated (e.g., via an engineered cysteine residue) to a functional moiety. Functional moieties are preferably attached to a portion of the polypeptide other than a binding site.

Exemplary functional moieties include affinity moieties, and effector moieties. Exemplary effector moieties include cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), PEG, or detectable molecules useful in imaging. In another embodiment, a polypeptide of the invention can be conjugated to a molecule that decreases vascularization of tumors. In other embodiments, the disclosed compositions may comprise polypeptides of the invention coupled to drugs or prodrugs. Still other embodiments of the present invention comprise the use of polypeptides of the invention conjugated to specific biotoxins or their cytotoxic fragments such as ricin, gelonin, *Pseudomonas* exotoxin or diphtheria toxin. The selection of which conjugated or unconjugated polypeptide to use will depend on the type and stage of cancer, use of adjunct treatment (e.g., chemotherapy or external radiation) and patient condition. It will be appreciated that one skilled in the art could readily make such a selection in view of the teachings herein.

Many effector molecules lack suitable functional groups to which binding polypeptides can be linked. In one embodiment, an effector molecule, e.g., a drug or prodrug is attached to the polypeptide through a linking molecule. In one embodiment, the linking molecule contains a chemical bond that allows for the activation of cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. Most preferably, the linking molecule comprises a disulfide bond or a thioether bond. In accordance with the invention, the linking molecule preferably comprises a reactive chemical group. Particularly preferred reactive chemical groups are N-succinimidyl esters and N-sulfosuccinimidyl esters. In a preferred embodiment, the reactive chemical group can be covalently bound to the effector via disulfide bonding between thiol groups. In one embodiment an effector molecule is modified to comprise a thiol group. One of ordinary skill in the art will appreciate that a thiol group contains a sulfur atom bonded to a hydrogen atom and is typically also referred to in the art as a sulfhydryl group, which can be denoted as "—SH" or "RSH."

In one embodiment, a linking molecule may be used to join an effector molecule with a polypeptide of the invention. The linking molecule may be cleavable or noncleavable. In one embodiment, the cleavable linking molecule is a redox-cleavable linking molecule, such that the linking molecule is cleavable in environments with a lower redox potential, such as the cytoplasm and other regions with higher concentrations of molecules with free sulfhydryl groups. Examples of linking molecules that may be cleaved due to a change in redox potential include those containing disulfides. The cleaving stimulus can be provided upon intracellular uptake of the binding protein of the invention where the lower redox potential of the cytoplasm facilitates cleavage of the linking molecule. In another embodiment, a decrease in pH triggers the release of the maytansinoid cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive linking molecules which may be used to target lysosomes or endosomes of cancer cells, include those with acid-cleavable bonds such as those found in acetals, ketals, orthoesters, hydrazones, trityls, cis-aconityls, or thiocarbamoyls (see for example, Willner et al., (1993), *Bioconj. Chem.*, 4: 521-7; U.S. Pat. Nos. 4,569,789, 4,631,190, 5,306,809, and 5,665,358). Other exemplary acid-sensitive linking molecules comprise dipeptide sequences Phe-Lys and Val-Lys (King et al., (2002), *J. Med. Chem.*, 45: 4336-43). The cleaving stimulus can be provided upon intracellular uptake trafficking to low pH endosomal compartments (e.g. lysosomes). Other exemplary acid-cleavable linking molecules are the molecules that contain two or more acid cleavable bonds for attachment of two or more maytansinoids (King et al., (1999), *Bioconj. Chem.*, 10: 27988; WO 98/19705).

Cleavable linking molecules may be sensitive to biologically supplied cleaving agents that are associated with a particular target cell, for example, lysosomal or tumor-associated enzymes. Examples of linking molecules that can be cleaved enzymatically include, but are not limited to, peptides and esters. Exemplary enzyme cleavable linking molecules include those that are sensitive to tumor-associated proteases such as Cathepsin B or plasmin (Dubowchik et al., (1999), *Pharm. Ther.*, 83: 67-123; Dubowchik et al., (1998), *Bioorg. Med. Chem. Lett.*, 8: 3341-52; de Groot et al., (2000), *J. Med. Chem.*, 43: 3093-102; de Groot et al., (1999)m 42: 5277-83). Cathepsin B-cleavable sites include the dipeptide sequences valine-citrulline and phenylalanine-lysine (Doronina et al., (2003), *Nat. Biotech.*, 21(7): 778-84); Dubowchik et al., (2002), *Bioconjug. Chem.*, 13: 855-69). Other exemplary enzyme-cleavable sites include those formed by oligopeptide sequences of 4 to 16 amino acids (e.g., Suc-β-Ala-Leu-Ala-Leu) which recognized by trouse proteases such as Thimet Oliogopeptidase (TOP), an enzyme that is preferentially released by neutrophils, macrophages, and other granulocytes.

VIII. Methods of Administration

Methods of preparing and administering polypeptides of the invention to a subject are well known to or are readily determined by those skilled in the art.

Compositions for administration to a subject include nucleic acid molecules which comprise a nucleotide sequence encoding a binding molecule of the invention (for gene therapy applications) as well as polypeptide molecules.

The route of administration of the polypeptides of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit which will preferably have labels or package inserts indicating that the associated compositions are useful for treating a subject suffering from, or predisposed to autoimmune or neoplastic disorders.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated.

Treatment dosages may be titrated using routine methods known to those of skill in the art to optimize safety and efficacy. In one embodiment, a polypeptide of the invention is one that has been previously administered to patients, but which has been modified to comprise a linker peptide of the invention in place of a traditional linker peptide. In such cases, the dosage of polypeptide administered will be consistent with that previously found to be safe and effective, i.e., the standard of care.

In one embodiment, the dosage can range, e.g., from about 1000 ug/kg to 0.1 ng/kg body weight. In one embodiment, the dosing range is 1 ug/kg to 100 ug/kg. In another embodiment, doses can range from. 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include administration on consecutive days, on alternate days or weekly.

Polypeptides of the invention can be administered on multiple occasions. Intervals between single dosages can be weekly, monthly or yearly. Intervals can also be irregular as indicated by measuring blood levels of polypeptide, polypeptide target, or antigen in the patient. In some methods, dosage is adjusted to achieve a plasma modified polypeptide concentration of 1-1000 µg/ml and in some methods 25-300 µg/ml. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of polypeptide per dose, with dosages of from 5 to 25 mg being more commonly used for radioimmunoconjugates and higher doses for cytotoxin-drug modified polypeptides) at relatively short intervals is sometimes required until progression of the disease is reduced or terminated, and preferably until the patient shows partial or complete amelioration of symptoms of disease. Thereafter, the patient can be administered a prophylactic regime.

It will further be appreciated that the molecules of the instant invention may be used in conjunction or combination with an agent or agents (e.g. to provide a combined therapeutic regimen). Exemplary agents with which a molecule of the invention may be combined include agents that represent the current standard of care for a particular disorder being treated. Such agents may be chemical or biologic in nature. The term "biologic" or "biologic agent" refers to any pharmaceutically active agent made from living organisms and/or their products which is intended for use as a therapeutic.

Polypeptides of the invention can optionally be administered in combination with other agents that are effective in treating the disorder or condition in need of treatment (e.g., prophylactic or therapeutic). As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. For example, chemotherapeutic or biologic agents could be administered in standard, well known courses of treatment in conjunction with the subject binding molecules. A skilled artisan (e.g. a physician) would be readily be able to discern effective combined therapeutic regimens without undue experimentation based on the selected adjunct therapy and the teachings of the instant specification.

In this regard it will be appreciated that the combination of the polypeptide and the agent may be administered in any order and within any time frame that provides a therapeutic benefit to the patient. That is, the agent and polypeptide may be administered in any order or concurrently. In yet other embodiments, the polypeptides and the chemotherapeutic treatment will be administered substantially simultaneously or concurrently. For example, the patient may be given the polypeptide while undergoing a course of chemotherapy. In preferred embodiments the polypeptide will be administered within 1 year of any agent or treatment. In other preferred embodiments the polypeptide will be administered within 10, 8, 6, 4, or 2 months of any agent or treatment. In still other preferred embodiments the polypeptide will be administered within 4, 3, 2 or 1 week of any agent or treatment. In yet other embodiments the polypeptide will be administered within 5, 4, 3, 2 or 1 days of the selected agent or treatment. It will further be appreciated that the two agents or treatments may be administered to the patient within a matter of hours or minutes (i.e. substantially simultaneously).

In one embodiment, a polypeptide can be produced in a patient by administration as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

The amount of agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., $9^{th}$ ed. 1996). In another embodiment, an amount of such an agent consistent with the standard of care is administered.

As previously discussed, the polypeptides of the present invention, may be administered in a pharmaceutically effective amount for the in vivo treatment of mammalian disorders. In this regard, it will be appreciated that the molecule of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a polypeptide of the invention, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the molecule of the invention may be administered to a human or other animal in accordance with the aforementioned methods of treatment in an amount sufficient to produce a therapeutic or prophylactic effect. In addition, a molecule of the invention may be used in an ex vivo therapy. A molecule of the invention can be administered to such human or other animal in a conventional dosage form prepared by combining the polypeptide with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides of the invention may prove to be particularly effective.

This invention is further illustrated by the following examples which should not be construed as limiting. The contents of all references, patents and published patent applications cited throughout this application are incorporated herein by reference.

EXAMPLES

Example 1

Traditional Gly/Ser Linkers are Targets for Xylose Addition

In order to confirm the identification of the novel post translational modification (PTM) of traditional linkers as xylose, the samples comprising traditional linkers (in this case a TNF-TWEAK bispecific antibody) were treated as follows.

To remove N-linked glycans (which would confound the analysis), the bispecific antibody was treated with PNGase F overnight, and the protein was then precipitated with ethanol. The O-linked carbohydrates were then released by resuspension of the pellets in 3M trifloroactic acid (TFA) and incubated at 100° C. for 5 hours. The released carbohydrate was fluorescently labeled by reductive amination with 2-aminobenzoic acid (2-AA) and sodium cyanoborhydride. Control reactions were also performed with solutions containing xylose, ribose, or buffer alone and all samples were cleaned up over GlcoClean S cartridges according to the manufacturers protocol prior to separation by HPLC.

The 2-AA labeled samples were analyzed on a Waters 2695 HPLC equipped with a 2475 fluorescence detector (excitation wavelength: 330 nm; emission wavelength: 420 nm). The labeled components were separated on a 4.6 mm×150 mm Asahipak NH2P-50-4D column at 0.75 mL/min at 30° C. with the following gradient conditions and Solvent A, 0.5 mM ammonium acetate, Solvent B, 0.25 M ammonium acetate, pH 5.0, Solvent C: acetonitrile, 0.1% of formic acid and 0.005% of heptafluorobutyric acid as shown below in Table 1:

| Time (min.) | % Solvent A | % Solvent B | % Solvent C |
|---|---|---|---|
| 0 | 80 | 20 | 0 |
| 40 | 30 | 30 | 40 |
| 50 | 0 | 75 | 25 |
| 51 | 80 | 20 | 0 |
| 91 | 80 | 20 | 0 |

The HPLC peaks were collected for identification using a Thermo Fisher Scientific LTQ FT Ultra Hybrid mass spectrometer, which was equipped with a nano-spray source. The instrument was operated in the positive mode. FTMS and FTMS/MS data were acquired. Table 2 shows the observed retention times of the main peak for each sample.

TABLE 2

| Sample | Retention time (min.) |
|---|---|
| Bispecific antibody with traditional linker | 38.56 |
| Xylose standard | 38.57 |
| Ribose standard | 40.07 |
| Buffer control | 35.99 |

As indicated in this table, the sugars released by acid hydrolysis of the Bispecific antibody closely matched the retention time of the xylose standard.

Analysis of the main peak by Fourier transform MS showed that the PTM of the Bispecific antibody was in fact a pentose sugar on the basis of molecular weight. The difference between the observed (obs.) and calculated m/z ratio as well as the measured error are all with specification for this instrument and are shown in Table 3.

TABLE 3

Protonated molecular ions of the collected HPLC peak and standards

| Sample | m/z (obs.) | m/z (cal.) | Error (ppm) |
|---|---|---|---|
| Bispecific antibody with traditional linker | 272.11306 | 272.11286 | 0.7 |
| Xylose standard | 272.11304 | 272.11286 | 0.6 |
| Ribose standard | 272.11303 | 272.11286 | 0.6 |

Analysis of the regimentation pattern observed by FT MS/MS revealed that the TNF-TWEAK BsAb closely resembled that of the xylose standard, and was clearly different from the ribose standard as shown in FIG. 1. These data taken with the similarity in retention time strongly indicate that the observed unusual PTM observed in the bispecific antibody comprising a traditional Gly-Ser linker was in fact due to covalent modification with xylose.

Example 2

Development and Optimization of a Tryptic Peptide Mapping Method

A tryptic peptide mapping method has been developed and optimized for characterization of anti-TNF-TWEAK bispecific protein, XWU198 RRS. All components in tryptic map with ion counts 2:2400 (2:1%, processed with BiopharmaLynx 1.1), were identified. Identified major peptides on the map accounted for 97% of the predicted sequences of the light chain and heavy chain plus scFv. Analysis of the lower-level peptides showed that both of the G4S linkers contain O-linked glycosaminoglycans (GAGs). The major form (~15%) is a single xylose linked to Ser461 or Ser466 within the first G4S linker, residues HC457-471. Longer GAG forms are also present, each at <1%. Approximately 4% of the second G4S linker, residues HC593-612, is modified with a single xylose. Sensitive sites for oxidation and deamidation have been identified: Asn323 and Asn392 in the heavy chain were susceptible to conversion to isoAsp through formation of succinimide; elevated levels of oxidation were observed in peptides containing Met34, Met83, Met112/Trp 115, Met260, and Met505 in the heavy chain and in the peptide containing Met4 in the light chain. There is also ~1.5% of the light chain having a serine at its N-terminus (from the signal peptide). No other abnormal components at levels ≥1% were identified.

Specifically, the protein (~65.4 μg) was reduced with 40 mM DTT in 6 M guanidine hydrochloride (GuHCl), 0.1 M Tris-HCl, pH 7.2, 5 mM EDTA, at 37° C. for 1.5 h. The reduced protein was alkylated by adding 5.0 μL of diluted 4-vinylpyridine (diluted 1:10 with 8 M GuHCl) to 50 μL of the sample solution; the resulting solution was kept at 25° C. in the dark for 45 min. The alkylated protein was recovered by precipitation with 1 mL of cooled ethanol. The solution was stored at −20° C. for 1 h and then centrifuged at 14000 g for 12 min at 4° C. The supernatant was discarded and the precipitate (~16.4 ug/vial) was washed once with cooled ethanol.

The reduced and alkylated protein (~16.4 μg, 162 pmols) was digested with 5% 5 (w/w) of trypsin (Promega) in 2 M urea, 0.1 M Tris-HCl, pH 7.5, 10 mM methylamine and 2 mM CaCl2 at 25° C. for 8 h. The final volume was 50 μL For N-deglycosylation, 1 μL of PNGase F (2.5 mU/μL, Glyko) was added to the digest at 6 h and the total tryptic digestion time was 8 h. An aliquot of 50 μL of 8 M urea was added to the digestion solution and then the solution was analyzed immediately or stored at −70° C. About 71 pmol of the digest was analyzed on an LC-MS system composed of an Acquity UPLC system and LCT Premier mass spectrometer (Waters Corp., Milford, Mass.). A 1.8-μm particle size, 2.1×150-mm Acquity HSS T3 C18 column (Cat#186003540, Waters) was used for separation of the digest.

The LC-MS data of tryptic peptide mapping of the parent molecule was processed using BioparmaLynx software (version 1.1). The resolution was set as 12000, ion intensity threshold was set to 100 counts and the minimum intensity threshold was set to 2,400 counts, which corresponds to detection of 0.5-1% of components. The amounts of modifications, such as oxidation, deamidation, glycation and O-glycosylation, etc, were estimated from EIC (extracted ion chromatograms) with MassLynx 4.1 software (see Table 2). 3.4 MSe (low and high energy collision) experiment.

About 62.5 pmol of the tryptic digest of the reduced parent molecule comprising GlySer linker was also analyzed on a Q-TOF Premier mass spectrometer coupled with an Acquity UPLC system. The separation of the digest was done as described above. The collision energy was set at 8 V for the first function and ramped from 25 to 45 V for the second function. MSe data were processed with BioPharmaLynx 1.2 (beta version, Build 14).

Figure 2:
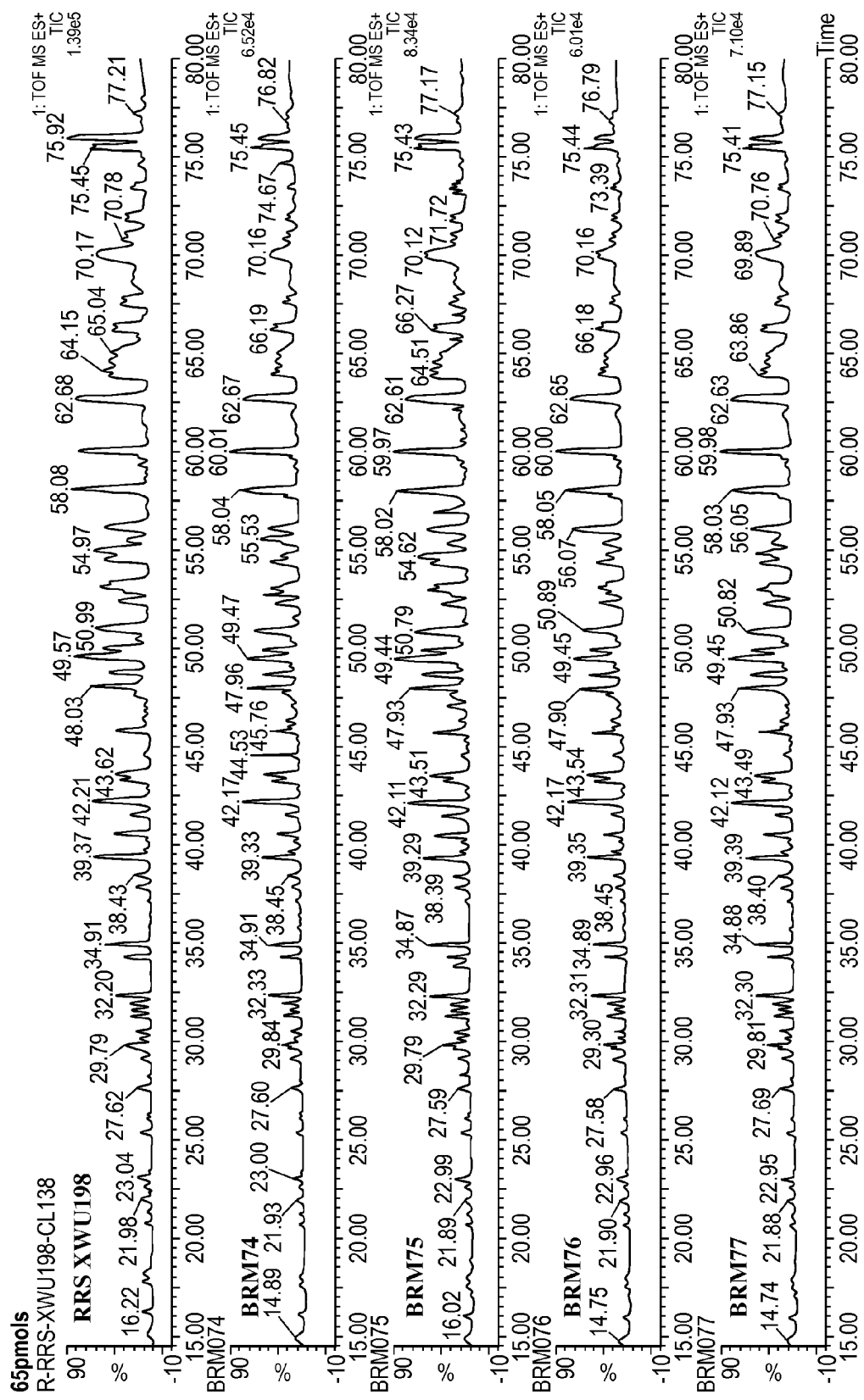
FIG. 2 shows tryptic peptide maps for molecules comprising traditional gly-ser linkers (panel a) and variant forms of gly-ser linkers (panels b-e) with identified components labeled on the map.

All the masses detected by the BiopharmaLynx software were verified and misassigned masses were corrected manually. All the unassigned components on the tryptic map were interpreted manually based on either accurate peptide masses or by MS/MS sequencing. FIG. 2a shows the tryptic peptide map for RRS with identified components labeled on the map; Table 4 lists the results. Peptides identified on the map accounted for 97% of the predicted sequences of the light chain and heavy chain plus scFv. Undetected peptides are small hydrophilic ones that were not retained on the column and presumably eluted with solvent. Based on detected peptide masses of the components in the peaks, the predicted sequence of the parent molecule was confirmed. In addition, there is also ~1.5% N+1 (Ser from the signal peptide) on the light chain. Table 4 is a compilation of the post-translational modifications to the (GGGGS)n linkers identified in RRS of XWUI98. Major potential O-glycosylation sites are Ser461 or Ser466. The major form of this modification is a single xylose), e.g., ~15% on the tryptic peptide residues 456-490 and ~4% of tryptic peptide, residues 570-630; however, longer length GAGs are also present at very low levels (<1% each) and were characterized based on accurate mass measurements and MS/MS sequencing). They include xylose-hexose2-hexuronicacid-HexNAC, xylose-hexose-hexose sulfatehexuronic acid-HexNAc and xylose-hexose-sialic acid. Sensitive sites for oxidation and deamidation have also been identified. Deamidation through formation of a succinimide was seen in the tryptic peptides containing N323 (~9.5%) and in the tryptic peptide containing residues N392/N397 (~7.5%) in the heavy chain. Sites that are susceptible to oxidation occur in both the LC and HC and include residues M4 (~5.7%) in the LC and M34 (~5%), M83 (~5.4%), M112/W115 (~14%), M260 (~8.6%), and residues M505 (~6%) in the He. Some of the deamidation and oxidation were probably derived from sample preparation. No other abnormal components at levels 2:1% were observed.

TABLE 4

| Tryp pept* | Residue # Start | Residue # End | RRT (Min) | Detected m/z | Detected Charge State | Detected Mass (Da) | Calculated Peptide Mass (DA) | Intensity (Counts) | Fragment Ions from MSe experiment | Modifiers |
|---|---|---|---|---|---|---|---|---|---|---|
| 1: T042 | 456 | 490 | 50.5 | 1277.2158 | 3 | 3828.6235 | 3828.5927 | 5829 | | Xylose, Hexose, Hexose sulfate, Hexuronic acid, HexNAC |
| 1: T042 | 456 | 490 | 50.5 | 1250.5679 | 3 | 3748.6797 | 3748.6405 | 4033 | | Xylose, 2 Hexose, Hexuronic acid, HexNAC |
| 1: T042 | 456 | 490 | 51.7 | 1167.208 | 3 | 3498.6001 | 3498.5716 | 7891 | | Xylose, Hexose, SA |
| 1: 1042 | 456 | 490 | 52.8 | 1060.1779 | 3 | 3177.5098 | 3177.4656 | 2821 | | 2 Xylose (#264 Da) |
| 1: T042* | 456 | 490 | 53.1 | 1016.1608 | 3 | 33045.4585 | 3045.4226 | 138057 | | Xylose (+132 Da) |
| 1: 1042 | 456 | 490 | 53.5 | 972.1456 | # | 2913.4128 | 2913.3811 | 988587 | b2; b3; b4; b5; b7; b8; b9; b10; b11; b12; b14; b15; b16; b17; b18; b19; b20; b21; b22; b23; b24; b26; b27; b28; y1; y2; y3; y4; y5; y6; y7; y8; y9; y10; y11; y12; y13; y14; y15; y16 | |
| 1: T050* | 570 | 630 | 63.4 | 1419.19 | 4 | 5672.528 | 5672.5146 | 3613 | | +1 Xylose |
| 1: T050 | 570 | 630 | 63.7 | 1386.1497 | 4 | 5540.5669 | 5540.5146 | 470211 | B3; b4; b7; b12; y1; y3; y4; y5; y6; y7; y8; 79; 711; y12 | |

*Pyridylethyl modified peptide

Example 2

Linker Peptides Lacking the Amino Acid Sequence GSG Reduce Xylose Addition

A proof of concept molecule was made comprising peptide linkers of the invention. The following sequences are provided below: Light Chain of XWU198 TNF-TWEAK (SEQ ID NO:23); Heavy Chain+scFv of XWU198 TNF-TWEAK for traditional G/S linkers (SEQ ID NO:24); Heavy Chain+scFv of BRM074 TNF-TWEAK for Test 074 (SEQ ID NO:25); Heavy Chain+scFv of BRM075 TNF-TWEAK for Test 075 (SEQ ID NO:26); Heavy Chain+scFv of BRM076 TNF-TWEAK for Test 076 (SEQ ID NO:27); and Heavy Chain+sdFv of BRM077 TNF-TWEAK for Test 077 (SEQ ID NO:28).

```
Sequences:

Light Chain of XWU198 TNF-TWEAK (applies to all five samples)
DVVMTQSPLS LPVTPGEPAS ISCRSSQSLV SSKGNTYLHW YLQKPGQSPQ LLIYKVSNRF

SGVPDRFSGS GSGTDFTLKI SRVEAEDVGV YYCSQSTHFP RTFGGGTKVE IKRTVAAPSV

FIFPPSDEQL KSGTASVVCL LNNFYPREAK VQWKVDNALQ SGNSQESVTE QDSKDSTYSL

SSTLTLSKAD YEKHKVYACE VTHQGLSSPV TKSFNRGEC

Heavy Chain + scFv of XWU198 TNF-TWEAK for traditional G/S linkers
EVQLVESGGG LVQPGGSLRL SCAASGFTFS RYAMSWVRQA PGKGLEWVAE ISSGGSYPYY
```

PDTVTGRFTI SRDNAKNSLY LQMNSLRAED TAVYYCARVL YYDYDGDRIE VMDYWGQGTL

VTVSSASTKG PSVFPLAPSS KSTSGGTAAL GCLVKDYFPE PVTVSWNSGA LTSGVHTFPA

VLQSSGLYSL SSVVTVPSSS LGTQTYICNV NHKPSNTKVD KKVEPKSCDK THTCPPCPAP

ELLGGPSVFL FPPKPKDTLM ISRTPEVTCV VVDVSHEDPE VKFNWYVDGV EVHNAKTKPR

EEQYNSTYRV VSVLTVLHQD WLNGKEYKCK VSNKALPAPI EKTISKAKGO PREPQVYTLP

PSRDELTKNQ VSLTCLVKGF YPSDIAVEWE SNGQPENNYK TTPPVLDSDG SFFLYSKLTV

DKSRWQQGNV FSCSVMHEAL HNHYTQKSLS LSPGKSGGGG SGGGGSGGGG SEVQLVESGG

GLVQPGGSLR LSCAASGFTF SDYAMHWVRQ APGKGLEWVS AISWNSGHID YADSVEGRFT

ISRDNAKNSL YLQMNSLRAE DTAVYYCAKV SYLSTASSLD YWGQGTLVTV SSGGGGSGGG

GSGGGGSGGG GSDIQMTQSP SSLSASVGDR VTITCRASQG IRNYLAWYQQ KPGKAPKLLI

YAASTRQSGV PSRFSGSGSG TDFTLTISSL QPEDEATYYC QRYNRAPYTF GQGTKVEIK

Heavy Chain + scFv of BRM074 TNF-TWEAK for Test 074
EVQLVESGGG LVQPGGSLRL SCAASGFTFS RYAMSWVRQA PGKGLEWVAE ISSGGSYPYY

PDTVTGRFTI SRDNAKNSLY LQMNSLRAED TAVYYCARVL YYDYDGDRIE VMDYWGQGTL

VTVSSASTKG PSVFPLAPSS KSTSGGTAAL GCLVKDYFPE PVTVSWNSGA LTSGVHTFPA

VLQSSGLYSL SSVVTVPSSS LGTQTYICNV NHKPSNTKVD KKVEPKSCDK THTCPPCPAP

ELLGGPSVFL FPPKPKDTLM ISRTPEVTCV VVDVSHEDPE VKFNWYVDGV EVHNAKTKPR

EEQYNSTYRV VSVLTVLHQD WLNGKEYKCK VSNKALPAPI EKTISKAKGQ PREPQVYTLP

PSRDELTKNQ VSLTCLVKGF YPSDIAVEWE SNGQPENNYK TTPPVLDSDG SFFLYSKLTV

DKSRWQQGNV FSCSVMHEAL HNHYTQKSLS LSPGKSGGG AGGGGAGGGG SEVQLVESGG

GLVQPGGSLR LSCAASGFTF SDYAMHWVRQ APGKGLEWVS AISWNSGHID YADSVEGRFT

ISRDNAKNSL YLQMNSLRAE DTAVYYCAKV SYLSTASSLD YWGQGTLVTV SSGGGGSGGG

GSGGGGSGGG GSDIQMTQSP SSLSASVGDR VTITCRASQG IRNYLAWYQQ KPGKAPKLLI

YAASTRQSGV PSRFSGSGSG TDFTLTISSL QPEDEATYYC QRYNRAPYTF GQGTKVEIK

R10-0182-TNF-TWEAK-MAP-21JUN10
3

Heavy Chain + scFv of BRM075 TNF-TWEAK for Test 075
EVQLVESGGG LVQPGGSLRL SCAASGFTFS RYAMSWVRQA PGKGLEWVAE ISSGGSYPYY

PDTVTGRFTI SRDNAKNSLY LQMNSLRAED TAVYYCARVL YYDYDGDRIE VMDYWGQGTL

VTVSSASTKG PSVFPLAPSS KSTSGGTAAL GCLVKDYFPE PVTVSWNSG LTSGVHTFPA

VLQSSGLYSL SSVVTVPSSS LGTQTYICNV NHKPSNTKVD KKVEPKSCDK THICPPCPAP

ELLGGPSVFL FPPKPKDTLM ISRTPEVTCV VVDVSHEDPE VKFNWYVDGV EVHNAKTKPR

EEQYNSTYRV VSVLTVLHQD WLNGKEYKCK VSNKALPAPI EKTISKAKGQ PREPQVYTLP

PSRDELTKNQ VSLTCLVKGF YPSDIAVEWE SNGQPENNYK TTPPVLDSDG SFFLYSKLTV

DKSRWQQGNV FSCSVMHEAL HNHYTQKSLS LSPGKSGGGG QGGGQGGGG SEVQLVESGG

GLVQPGGSLR LSCAASGFTF SDYAMHWVRQ APGKGLEWVS AISWNSGHID YADSVEGRFT

ISRDNAKNSL YLQMNSLRAE DTAVYYCAKV SYLSTASSLD YWGQGTLVTV SSGGGGSGGG

GSGGGGSGGG GSDIQMTQSP SSLSASVGDR VTITCRASQG IRNYLAWYQQ KPGKAPKLLI

YAASTRQSGV PSRFSGSGSG TDFTLTISSL QPEDEATYYC QRYNRAPYTF GQGTKVEIK

Heavy Chain + scFv of BRM076 TNF-TWEAK for Test 076
EVQLVESGGG LVQPGGSLRL SCAASGFTFS RYAMSWVRQA PGKGLEWVAE

Sequences:

```
PDTVTGRFTI SRDNAKNSLY LQMNSLRAED TAVYYCARVL YYDYDGDRIE VMDYWGQGTL

VTVSSASTKG PSVFPLAPSS KSTSGGTAAL GCLVKDYFPE PVTVSWNSGA LTSGVHTFPA

VLQSSGLYSL SSVVTVPSSS LGTQTYICNV NHKPSNTKVD KKVEPKSCDK THICPPCPAP

ELLGGPSVFL FPPKPKDTLM ISRTPEVTCV VVDVSHEDPE VKFNWYVDGV EVHNAKTKPR

EEQYNSTYRV VSVLTVLHQD WLNGKEYKCK VSNKALPAPI EKTISKAKGQ PREPQVYTLP

PSRDELTKNQ VSLTCLVKGF YPSDIAVEWE SNGQPENNYK TIPPVLDSDG SFFLYSKLTV

DKSRWQQGNV FSCSVMHEAL HNHYTQKSLS LSPGKSGGGP SGGGPSGGGG SEVQLVESGG

GLVQPGGSLR LSCAASGFTF SDYAMHWVRQ APGKGLEWVS AISWNSGHID YADSVEGRFT

ISRDNAKNSL YLQMNSLRAE DTAVYYCAKV SYLSTASSLD YWGQGTLVTV SSGGGGSGGG

GSGGGGSGGG GSDIQMTQSP SSLSASVGDR VTITCRASQG IRNYLAWYQQ KPGKAPKLLI

YAASTRQSGV PSRFSGSGSG TDFTLTISSL QPEDEATYYC QRYNRAPYTF GQGTKVEIK

Heavy Chain + sdFv of BRM077 TNF-TWEAK for Test 077
EVQLVESGGG LVQPGGSLRL SCAASGFTFS RYAMSWVRQA PGKGLEWVAE ISSGGSYPYY

PDTVTGRFTI SRDNAKNSLY LQMNSLRAED TAVYYCARVL YYDYDGDRIE VMDYWGQGTL

VTVSSASTKG PSVFPLAPSS KSTSGGTAAL GCLVKDYFPE PVTVSWNSGA LTSGVHTFPA

FLQSSGLYSL SSVVTVPSSS LGTQTYICNV NHKPSNTKVD KKVEPKSCDK THTCPPCPAP

ELLGGPSVFL FPPKPKDTLM ISRTPEVTCV VVDVSHEDPE VKFNWYVDGV EVHNAKTKPR

EEQYNSTYRV VSVLTVLHQD WLNGKEYKCK VSNKALPAPI EKTISKAKGQ PREPQVYTLP

PSRDELTKNQ VSLTCLVKGF YPSDIAVEWE SNGQPENNYK TTPPVLDSDG SFFLYSKLTV

DKSRWQQGNV FSCSVMHEAL HNHYTQKSLS LSPGKSGGG SPGGGSPGGG SEVQLVESGG

GLVQPGGSLR LSCAASGFTF SDYAMHWVRQ APGKGLEWVS AISWNSGHID YADSVEGRFT

ISRDNAKNSL YLQMNSLRAE DTAVYYCAKV SYLSTASSLD YWGQGTLVTV SSGGGGSGGG

GSGGGGSGGG GSDIQMTQSP SSLSASVGDR VTITCRASQG IRNYLAWYQQ KPGKAPKLLI

YAASTRQSGV PSRFSGSGSG TDFTLTISSL QPEDEATYYC QRYNRAPYTF GQGTKVEIK
```

The test 074 molecule comprises the linker (GGGGA)2GGGGS (SEQ ID NO:8); the test 075 molecule comprises the linker (GGGGQ)2GGGGS (SEQ ID NO:5); the test 076 molecule comprises the linker (GGGPS)2GGGGS (SEQ ID NO:6); and the test 077 molecule comprises the linker GGGGS(PGGGS)2 (SEQ ID NO:7). All proteins were expressed in CRG cells. Linker I is the linker between the Fc and the scFv, and linker 2 is the linker between the V domains of the scFv molecule. In this experiment, linker 2 is a traditional G/S linker for all samples.

Figure 3A:
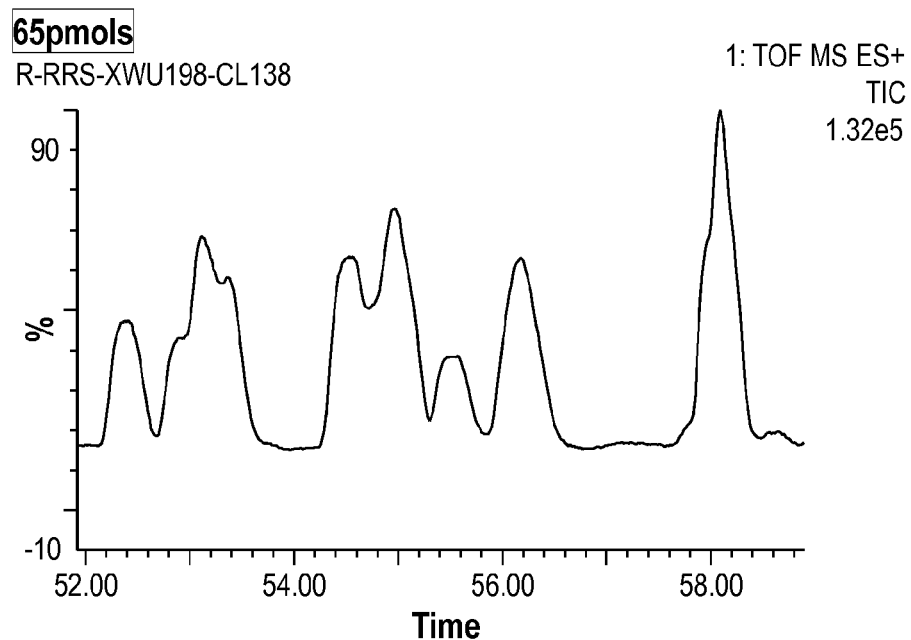
FIG. 3 shows extracted ion chromatograms (EIC) of major tryptic peptides containing Linker 1 (between the Fc and the scFv of a binding molecule) from both Anti-TNF-TWEAK RRS wt shown in FIG. 3, panels a-e, and the BRM074 Linker 1 mutant in FIG. 3, panels f-i. Panel (a) shows a TIC trace between 52 and 59 minutes in the tryptic peptide map of Anti-TNF-TWEAK RRS wt (a-e), (b) EIC of the peptide corresponding to predicted residues 456-490 (2913.3813 Da) containing unmodified G4S Linker 1; (c) spectrum at 55 min showing isotopic peaks for the triply-charged mass 972.1295$^{+3}$ for the unmodified peptide; (d) EIC of the peptide corresponding to residues 456-490 containing the G4S Linker 1 with a single xylose modification (3045.4236 Da); (e) spectrum at 54.6 min showing isotopic peaks for the triply-charged mass m/z=1016.1534$^{+3}$ for singly xylosylated peptide; (f) TIC trace of the tryptic peptide map of the Linker mutant BRM074 between 52 and 59 minutes, (g) EIC of the peptide corresponding to residues 456-490 with BRM074 mutations (2881.3914 Da); (h) spectrum at 55.6 min showing isotopic peaks of m/z=961.4722$^{+3}$ for the BRM074 mutant peptide; and (i) polypeptide residues corresponding residues 456-490 containing BRM074 mutations plus xylose (calculated mass 3021.434 Da) was not detected in the map; as shown, there is no peak in the EIC for m/z (z=+3)=1013.13.
Figure 3B:
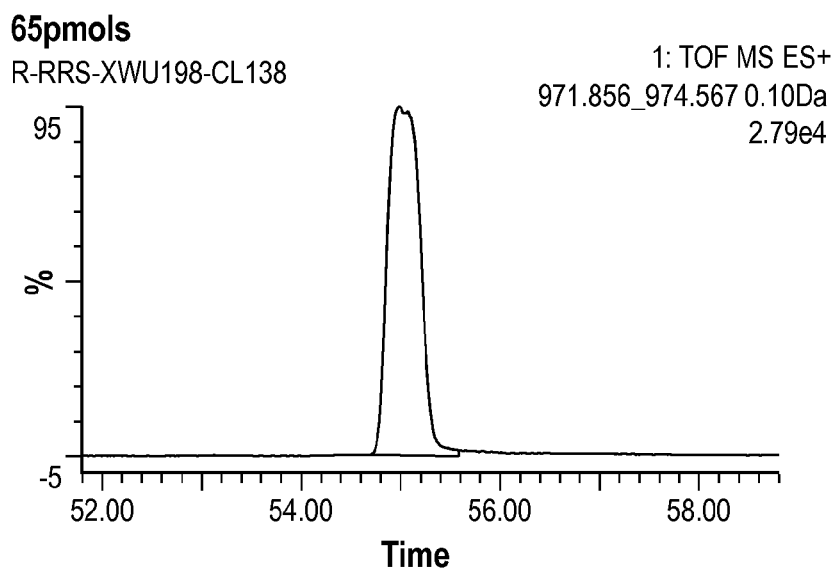
Figure 3C:
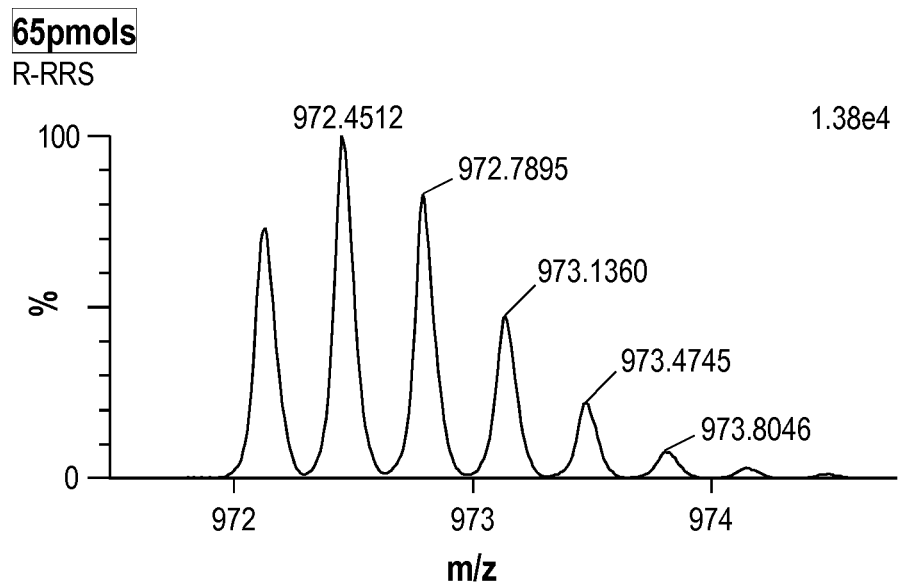
Figure 3D:
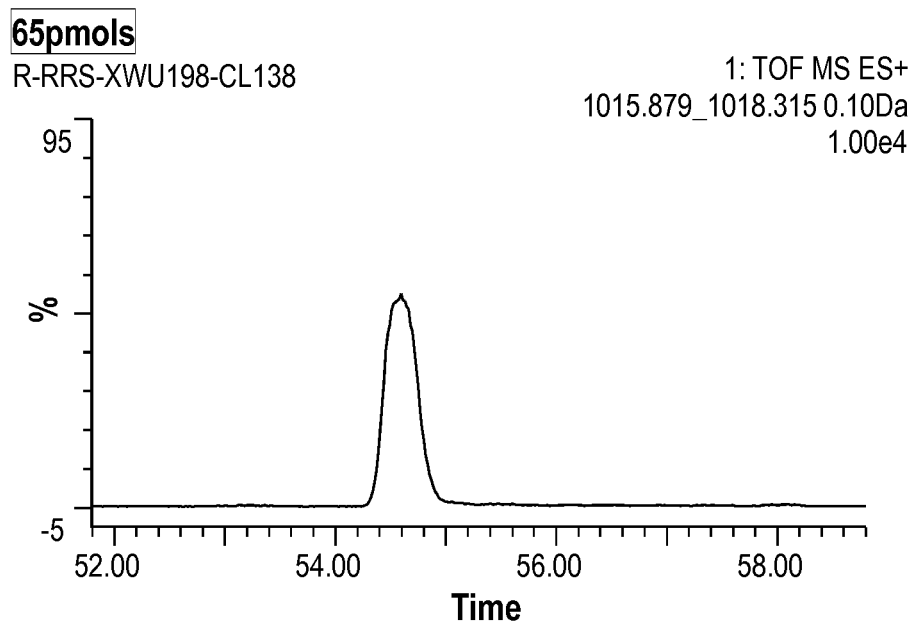
Figure 3E:
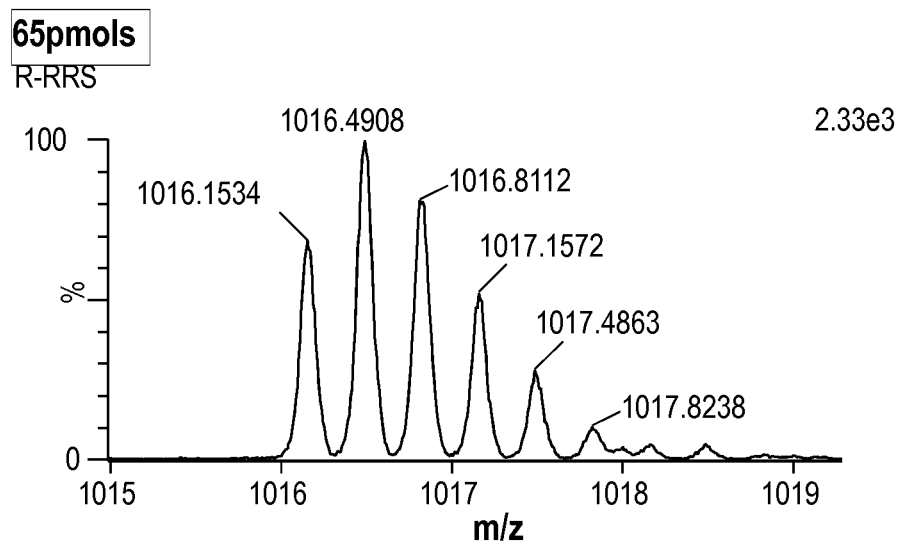
Figure 3F:
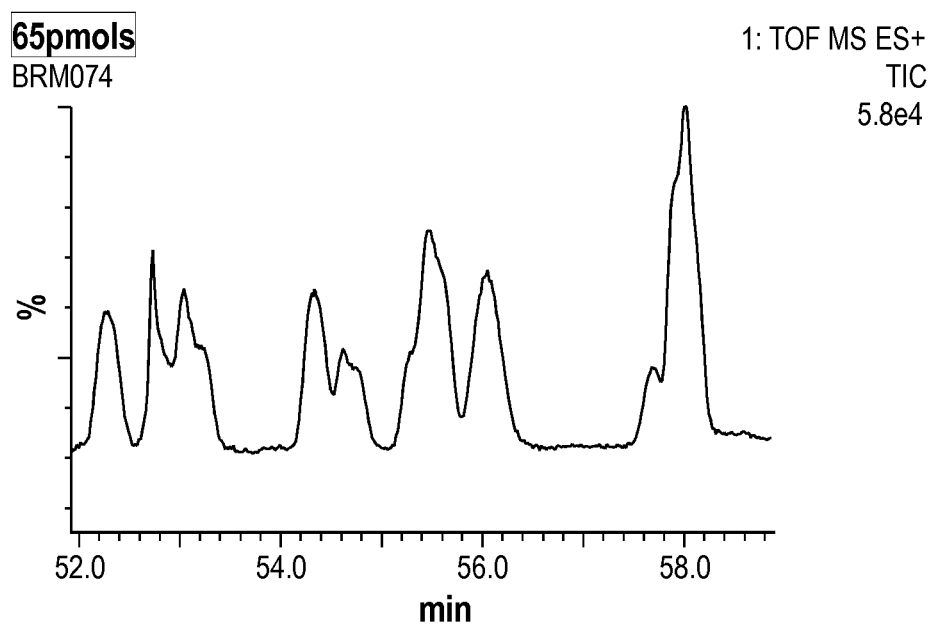
Figure 3G:
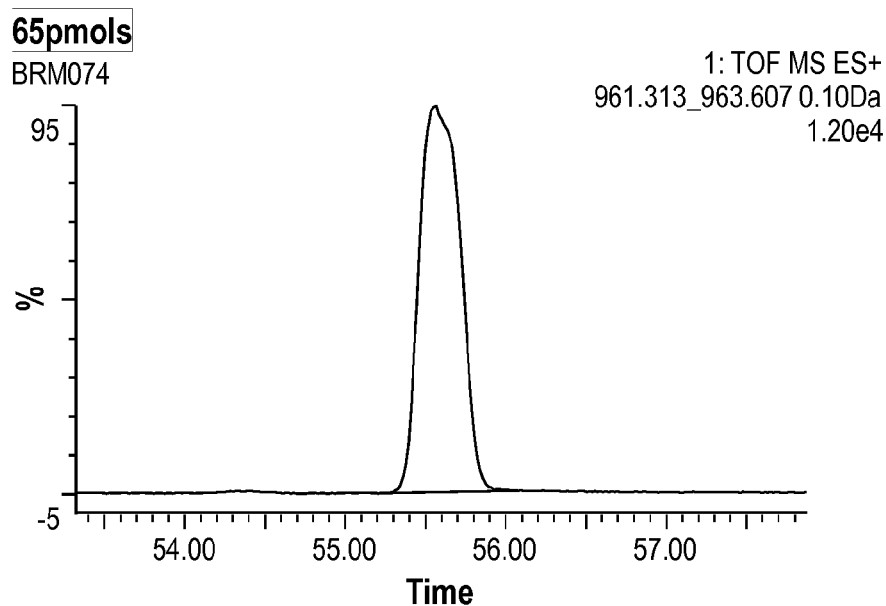
Figure 3H:
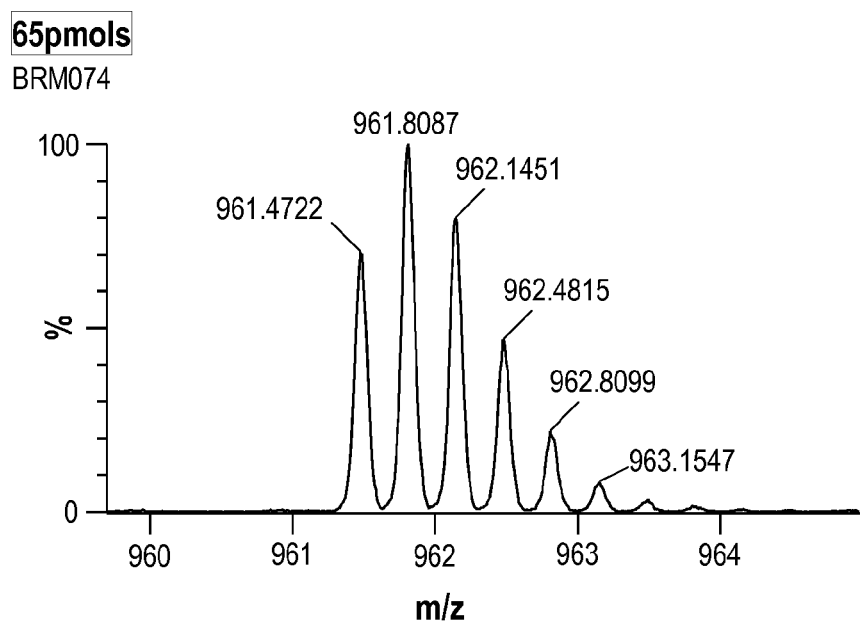
Figure 3:
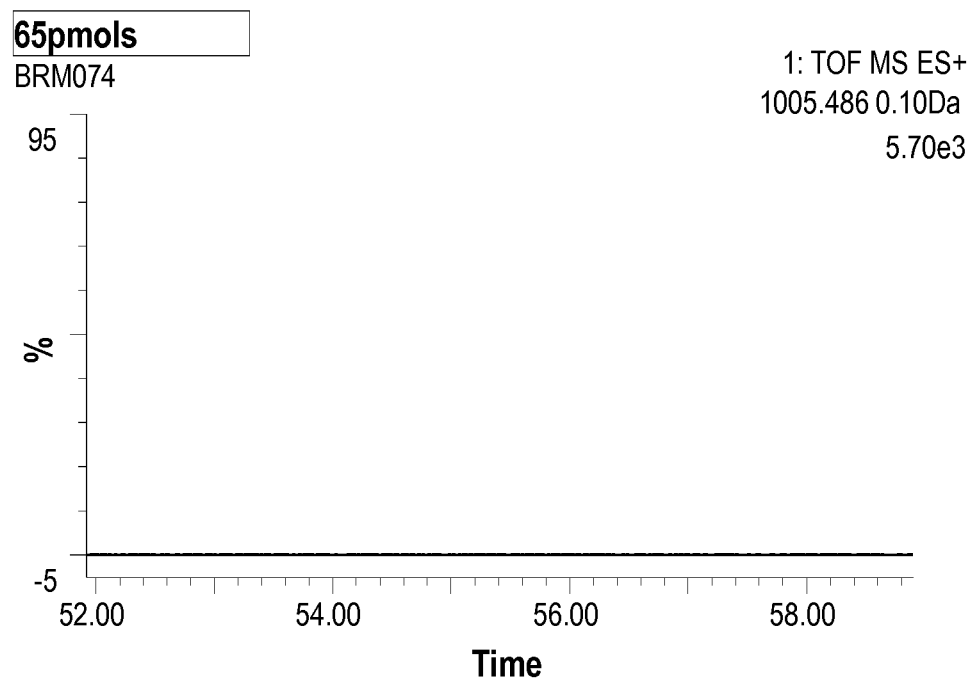

Using Mass Spectrometry, in the control molecule xylose was detected on both linker I and linker 2. The TIC chromatograms are shown if FIG. 2 panels b-e. In each case, the peptide containing the modified linker I between the FC and scFv domains (aa 456-490) could be unambiguously identified and the levels of xylosylation determined. FIG. 3a shows a comparison between the original molecule comprising an unmodified linker and test BRM074. As shown in the Figure, replacement of the modified serine residues with alanine completely eliminates the glycosylation in this peptide.

The total levels of modification for the parental molecule comprising an unmodified liner and test molecules 074, 075, 076, and 077 are summarized in Table 5. Replacement of the serines in linker 1 with either alanine (074) or glutamine (075) completely eliminates xylosylation of this sequence. Substitution of a proline for a glycine immediately amino-terminal to the modified serines (076) reduced, but did not eliminate this modification, while the same substitution on the carboxy-terminal side (077) eliminated the xylosylation. The unmodified linker 2 sequence was glycosylated to a similar extent as the parental molecule as expected. Thus, where the linker peptides of the invention were included (i.e., at linker 1) the percentage of molecules on which xylose was detected on that linker 1 was decreased in every instance.

Example 3

Polypeptides Comprising Linker Peptides Lacking the Amino Acid Sequence GSG Exhibit Reduced Aggregation The test molecules 074, 075, 076, 077, and the parental TNF-TWEAK molecule were purified by conventional methods used for monoclonal antibodies. All five constructs were expressed in transfected DG44i CHO cells that had been FACS-sorted for higher expression, and the cell culture medium harvested for purification of the bispecifics. Each culture supernatant was passed through a protein A affinity column and bound bispecific antibody was eluted with low pH glycine buffer. Protein A chromatography eluates were neutralized using basic Tris buffer, and the samples assayed both by gel electrophoresis (SDS-PAGE) and analytical size exclusion chromatography (SEC).

For parental and the 074, 076 and 077 test molecules, reducing and non-reducing SDS-PAGE analysis shows the expected species, with a heavy chain+linker+scFv chain of ~75 kDa and a ~25 kDa light chain. The 075 test molecule, which contains serine to glutamine substitutions in linker 1, shows the two expected species, along with a ~50 kDa species. This latter species is consistent in size with a heavy chain from which the scFv has been cleaved via proteolysis in linker 1.

Parental and test molecules 074, 076 and 077 were all monodisperse by analytical SEC, and eluted at positions consistent with monomeric bispecific antibodies of ~200 kDa. 075 shows the expected species, as well as a species that elutes at a later position, consistent with the truncated, scFv-deficient form observed by SDS-PAGE. In addition, while the parental samples typically contain between 6-8% aggregate, principally in the form of dimers, test molecules 074, 075, 076 and 077 contained 0, 2, 2 and 0% aggregate, respectively.

| Construct | % Monomer | % Aggregate |
|---|---|---|
| XWU198 (parental) | 92-94 | 6-8 |
| BRM074 | 100 | 0 |
| BRM075 | 98 | 2 |
| BRM076 | 98 | 2 |
| BRM077 | 100 | 0 |

Example 4

Polypeptides Comprising Modified Linkers have Increased pH Stability

The samples, EI04 wild type, 7.0 mg/mL in 10 mM Na Citrate, 150 mM NaCl, pH 6.0 (Lot# NB 14779-58) and EI04linker mutant, 2.6 mg/mL at 10 mM Na Citrate, 150 mg/mL NaCl, pH 6.0 (Lot# NB15185-81) were placed into $Na_2HPO_4$/citric acid buffer at a variety of pHs, specifically at pH 5.5, 6.0, 7.0, 8.0 and the protein concentration was adjusted to 1.0 mg/mL.

The samples were subjected to stress conditions: Isothermal Incubation at 40° C. with time points taken at Time 0, Time 2 wks, and Time 4 wks.

A variety of assays were performed using standard methods to evaluate the integrity of the protein samples: SEC-HPLC, SDS-PAGE, Turbidity/Opalescence, and CE-SDS.

Figure 4A:
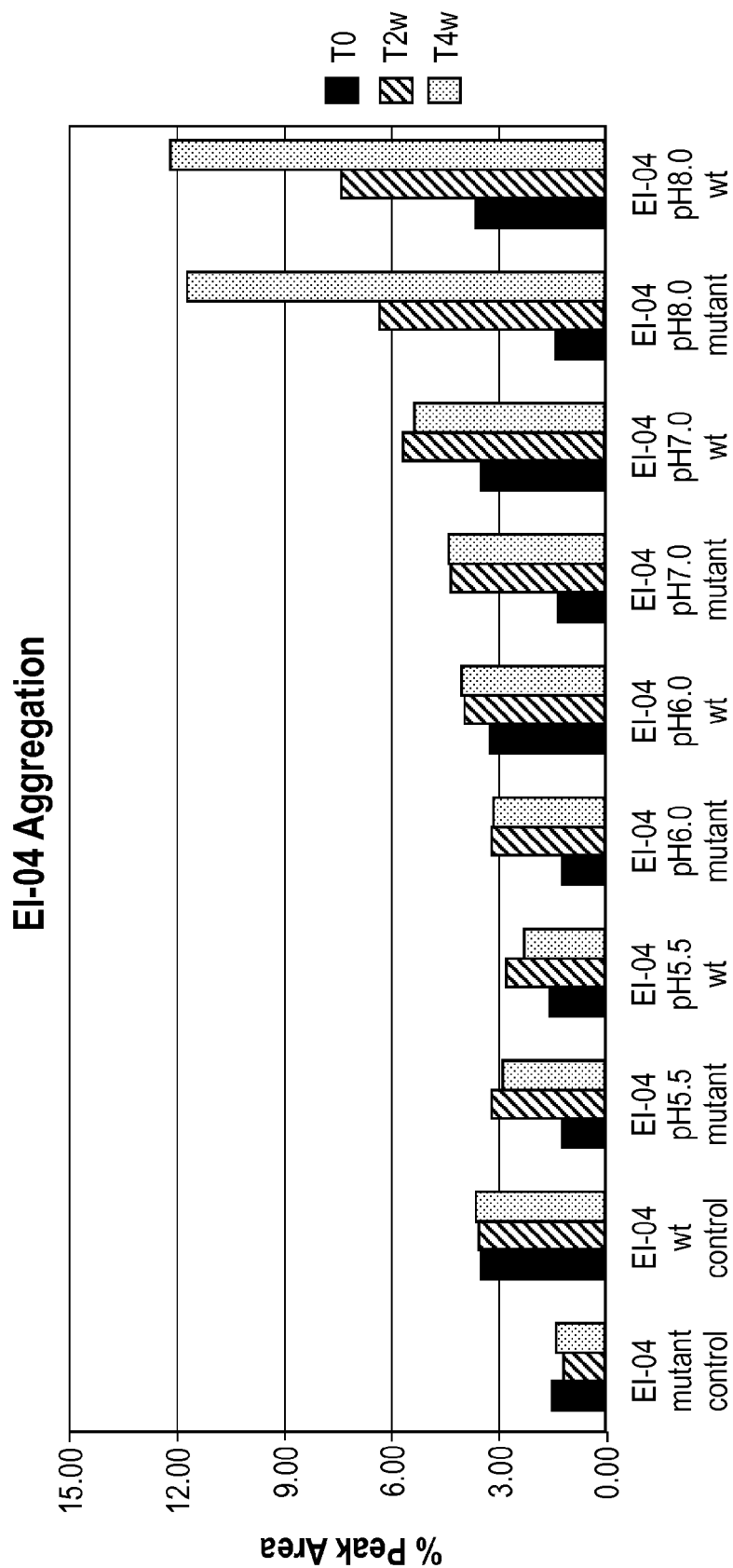
FIG. 4 shows that under stress conditions, the polypeptides comprising the linker mutants and the wild type linkers exhibited similar aggregation levels (panel a). However, the linker mutant samples showed lower levels of fragments at pH 8.0 at 40° C. over 2 weeks compared to the wild-type samples (panel B).
Figure 4A:
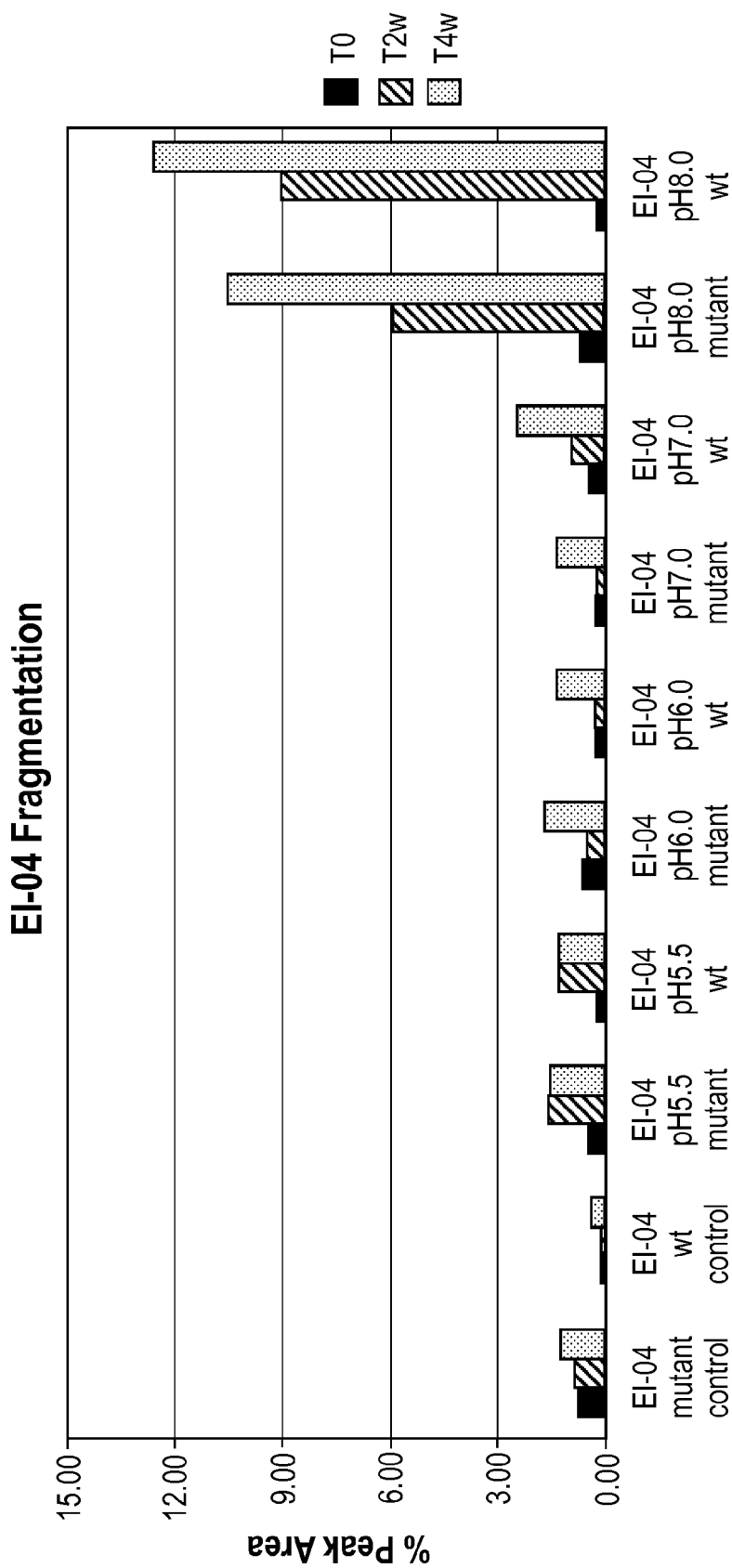
Figure 5A:
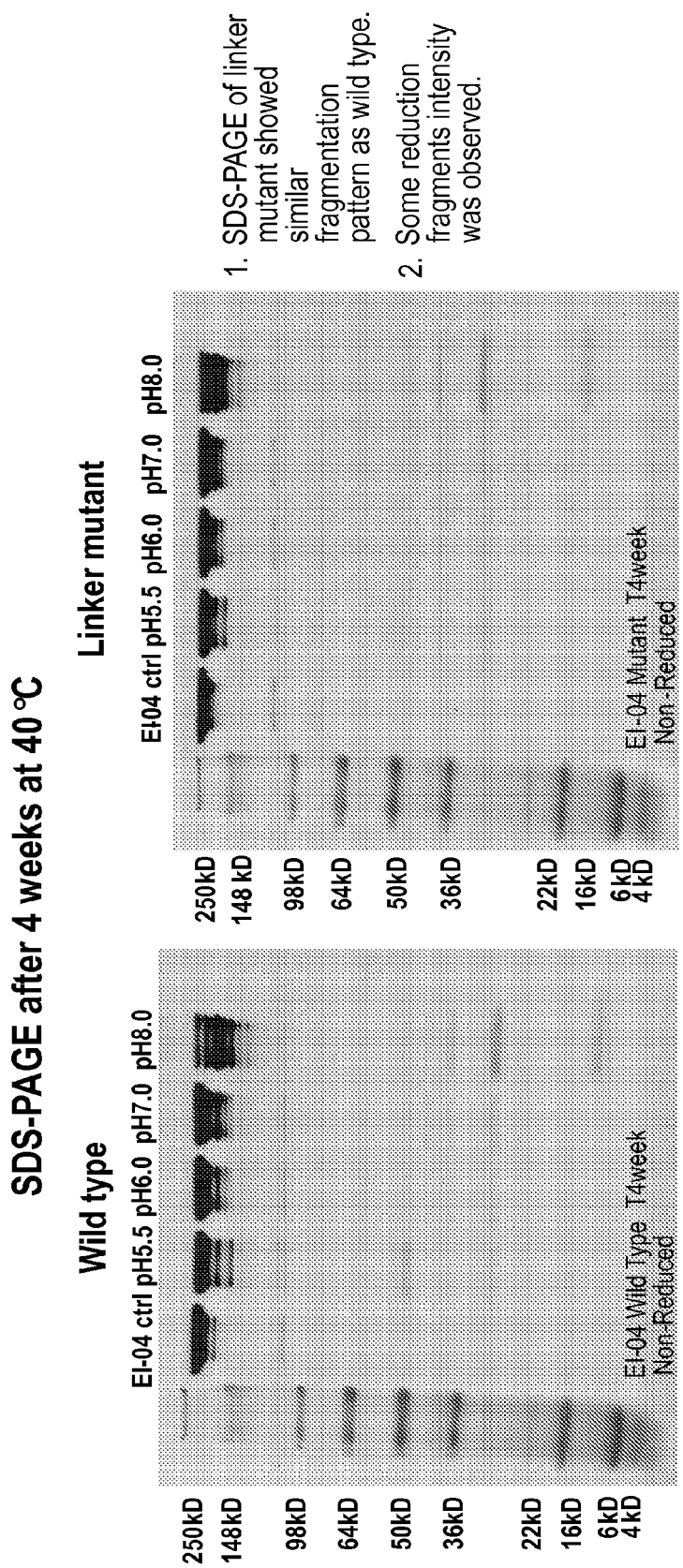
FIG. 5 shows SDS-PAGE analysis confirming similar fragmentation patterns were evident between linker mutant samples and wild-type samples, but some reduction in fragment intensity was observed in the mutant samples. Panel A and B show non-reduced samples and panels C and D, reduced samples.
Figure 5B:
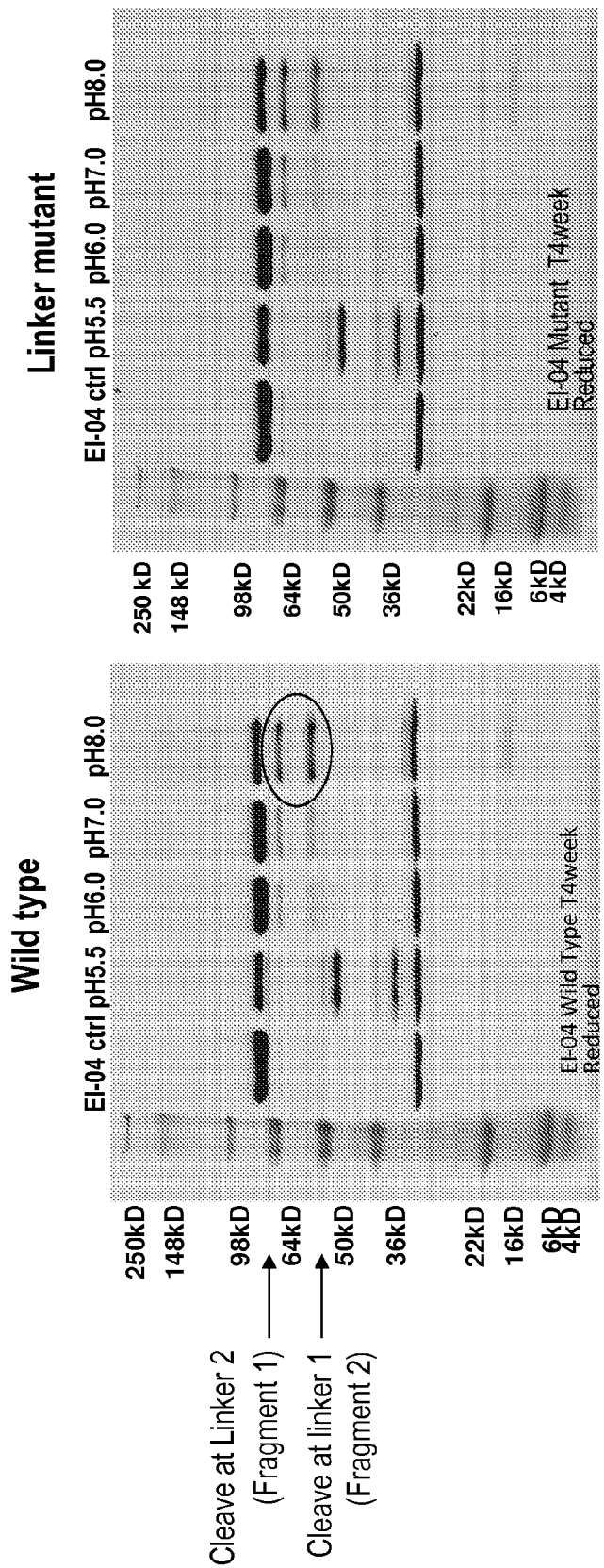
Figure 6:
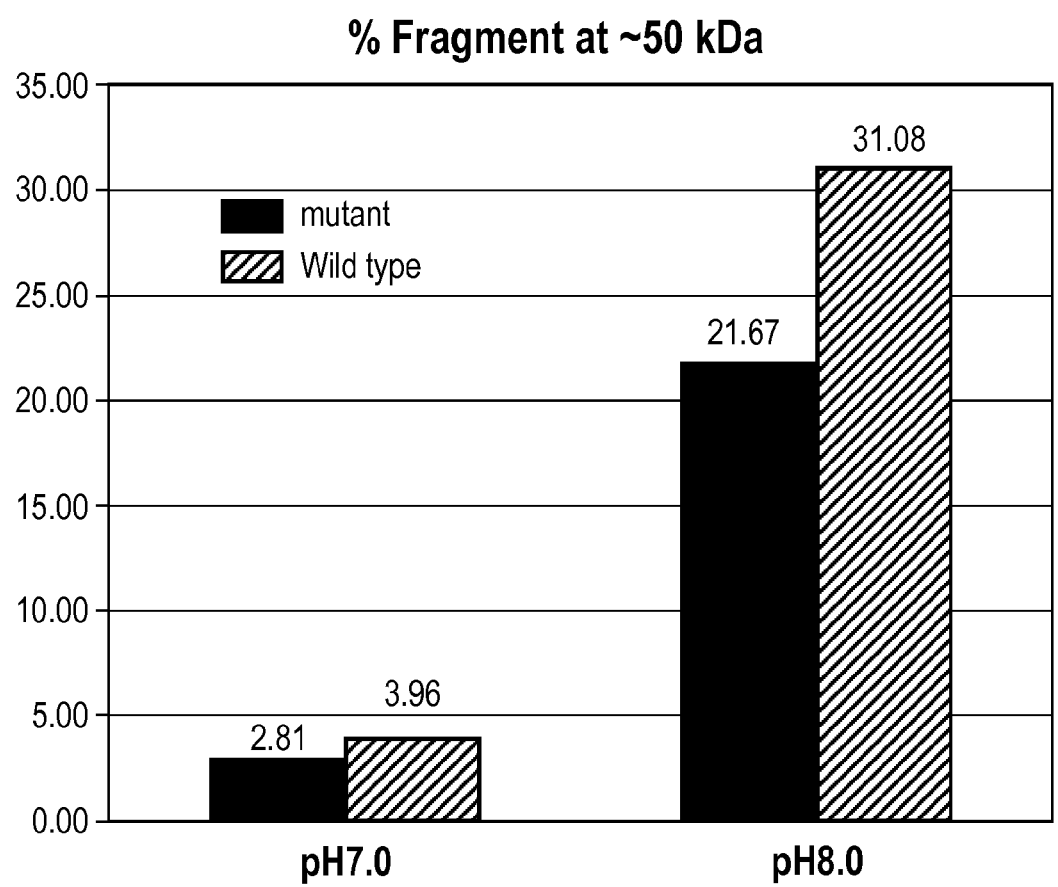
FIG. 6 shows CE-SDS analysis and confirms the reduction in the percentage of fragments migrating at approximately 50 kD present in the mutant linker samples as compared to the wild-type samples.

Under these stress conditions, the polypeptides comprising the linker mutants and the wild type linkers exhibited similar aggregation levels. However, the linker mutant samples showed lower levels of fragments at pH 8.0 at 40° C. over 2 weeks compared to the wild-type samples (FIG. 4). Using SDS-PAGE analysis, similar fragmentation patterns were evident between linker mutant samples and wild-type samples, but some reduction in fragment intensity was observed in the mutant samples (FIG. 5). CE-SDS analysis confirmed the reduction in the percentage of fragments migrating at approximately 50 kD present in the mutant linker samples as compared to the wild-type samples (FIG. 6).

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 5

O-linked xylosylation on linkers in cell lines from constructs TNF/TWEAK RRS XWU198-CL138 (14125-52), BRM074 (13502-82), BRM075 (13502-78), BRM076 (NB13502-87), and BRM077 (13502-73).

| Construct | Linker | % 1x Xyl | % 2xXyl | % Xyl-Hex | % Xyl-Hex-SA | % Xyl-2Hex-HexA | % Xyl-2Hex-HexA-HexNAc | % Xyl-Hex-Hex sulfate-HexA-HexNAc | O-glycans Linker (%) | Chain w/O-glycans (%) | Protein w/O-glycans (%) |
|---|---|---|---|---|---|---|---|---|---|---|---|
| RRS | 1 | 14.48 | 0.51 | 1.13 | 1.33 | 0.47 | 0.61 | 0.90 | 19.43 | 22.23 | 39.52 |
| XWU198 | 2 | 3.47 | 0.00 | 0.00 | 0.00 | 0.00 | 0.00 | 0.00 | 3.47 | | |
| BRM074 | 1 | 0.00 | 0.00 | 0.00 | 0.00 | 0.00 | 0.00 | 0.00 | 0.00 | 4.47 | 8.73 |
| | 2 | 4.47 | 0.00 | 0.00 | 0.00 | 0.00 | 0.00 | 0.00 | 4.47 | | |
| BRM075 | 1 | 0.00 | 0.00 | 0.00 | 0.00 | 0.00 | 0.00 | 0.00 | 0.00 | 5.60 | 10.89 |
| | 2 | 5.60 | 0.00 | 0.00 | 0.00 | 0.00 | 0.00 | 0.00 | 5.60 | | |
| BRM076 | 1 | 2.10 | 0.00 | 0.00 | 0.00 | 0.00 | 0.00 | 0.00 | 2.10 | 8.03 | 15.42 |
| | 2 | 6.06 | 0.00 | 0.00 | 0.00 | 0.00 | 0.00 | 0.00 | 6.06 | | |
| BRM077 | 1 | 0.00 | 0.00 | 0.00 | 0.00 | 0.00 | 0.00 | 0.00 | 0.00 | 6.11 | 11.85 |
| | 2 | 6.11 | 0.00 | 0.00 | 0.00 | 0.00 | 0.00 | 0.00 | 6.11 | | |

\* Chain with at least an O-glycan (%) = (1 − (1 − % Linker1/100) × (1 − % Linker2/100)) × 100%
Protein with at least an O-glycan (%) = (1 − (1 − % O-glycans per chain/100)$^2$) × 100%

What is claimed is:

1. A polypeptide comprising a linker peptide, wherein the linker peptide lacks the sequence GSG and comprises an amino acid sequence selected from the group consisting of:
   (a) (GGGGA)$_2$GGGGS (SEQ ID NO:8),
   (b) (GGGGQ)$_2$GGGGS (SEQ ID NO:5),
   (c) (GGGPS)$_2$GGGGS (SEQ ID NO:6), and
   (d) GGGGS(PGGGS)$_2$ (SEQ ID NO:7).

2. The polypeptide of claim 1, wherein the linker peptide consists of an amino acid sequence selected from the group consisting of:
   (a) (GGGGA)$_2$GGGGS (SEQ ID NO:8);
   (b) (GGGGQ)$_2$GGGGS (SEQ ID NO:5);
   (c) (GGGPS)$_2$GGGGS (SEQ ID NO:6); and
   (d) GGGGS(PGGGS)$_2$ (SEQ ID NO:7).

3. The polypeptide of claim 1, wherein the linker peptide is genetically fused to an Fc moiety.

4. The polypeptide of claim 1, wherein the linker peptide is interposed between two polypeptide domains, wherein at least one of the polypeptide domains comprises a VH domain, a VL domain, a scFv molecule, an Fc moiety, a receptor or extracellular domain thereof, an Fab, and a receptor binding portion of a ligand, an enzyme, a growth factor, an interleukin, a cytokine, or a chemokine.

5. The polypeptide of claim 3, wherein the Fc moiety is an Fc region.

6. The polypeptide of claim 3, wherein the Fc moiety is an scFc region.

7. The polypeptide of claim 1, wherein the polypeptide is a bispecific antibody molecule.

8. A composition comprising the polypeptide of claim 1 and a pharmaceutically acceptable carrier.

9. A binding molecule comprising an scFv moiety and an Fc moiety, wherein the scFv moiety and the Fc moiety are genetically linked by a linker peptide, wherein the linker peptide comprises an amino acid sequence selected from the group consisting of:
   (a) (GGGGA)$_2$GGGGS (SEQ ID NO: 8),
   (b) (GGGGQ)$_2$GGGGS (SEQ ID NO:5),
   (c) (GGGPS)$_2$GGGGS (SEQ ID NO:6), and
   (d) GGGGS(PGGGS)$_2$ (SEQ ID NO:7),
and wherein the linker peptide lacks the sequence GSG.

10. The binding molecule of claim 9, wherein the linker peptide consists of an amino acid sequence selected from the group consisting of:
   (a) (GGGGA)$_2$GGGGS (SEQ ID NO:8),
   (b) (GGGGQ)$_2$GGGGS (SEQ ID NO:5), (c) (GGGPS)₂GGGGS (SEQ ID NO:6), and
(d) GGGGS(PGGGS)₂ (SEQ ID NO:7).

11. A composition comprising the binding molecule of claim 9 and a pharmaceutically acceptable carrier.

12. An scFv molecule comprising a VH and a VL region, wherein the VH and VL region are genetically linked by a linker peptide, wherein the linker peptide comprises an amino acid sequence selected from the group consisting of:
(a) (GGGGA)₂GGGGS (SEQ ID NO:8);
(b) (GGGGQ)₂GGGGS (SEQ ID NO:5);
(c) (GGGPS)₂GGGGS (SEQ ID NO:6);
(d) GGGGS(PGGGS)₂ (SEQ ID NO:7);
(e) (GGGGA)₃ (SEQ ID NO:12); and
(f) (GGGGA)₄ (SEQ ID NO:13),
and wherein the linker peptide lacks the sequence GSG.

13. The scFv molecule of claim 12, wherein the linker peptide consists of an amino acid sequence selected from the group consisting of:
(a) (GGGGA)₂GGGGS (SEQ ID NO:8);
(b) (GGGGQ)₂GGGGS (SEQ ID NO:5);
(c) (GGGPS)₂GGGGS (SEQ ID NO:6);
(d) GGGGS(PGGGS)₂ (SEQ ID NO:7);
(e) (GGGGA)₃ (SEQ ID NO:12); and
(f) (GGGGA)₄ (SEQ ID NO:13).

14. A composition comprising the scFv molecule of claim 12 and a pharmaceutically acceptable carrier.

15. A binding molecule comprising an scFv moiety which comprises a VH and a VL region and an Fc moiety, wherein the scFv moiety and the Fc moiety are genetically linked by a first linker peptide consisting of an amino acid sequence selected from the group consisting of:
(a) (GGGGA)₂GGGGS (SEQ ID NO: 8);
(b) (GGGGQ)₂GGGGS (SEQ ID NO:5),
(c) (GGGPS)₂GGGGS (SEQ ID NO:6), and
(d) GGGGS(PGGGS)₂ (SEQ ID NO:7),
and the VH and the VL region are genetically linked by a second linker peptide consisting of an amino acid sequence selected from the group consisting of:
(e) (GGGGA)₃ (SEQ ID NO:12); and
(f) (GGGGA)₄ (SEQ ID NO:13).

16. A composition comprising the binding molecule of claim 15 and a pharmaceutically acceptable carrier.

17. A linker peptide selected from the group consisting of:
(a) a linker peptide comprising the amino acid sequence (GGGGA)₂GGGGS (SEQ ID NO:8);
(b) a linker peptide comprising the amino acid sequence (GGGGQ)₂GGGGS (SEQ ID NO:5);
(c) a linker peptide comprising the amino acid sequence (GGGPS)₂GGGGS (SEQ ID NO:6);
(d) a linker peptide comprising the amino acid sequence GGGGS(PGGGS)₂ (SEQ ID NO:7);
(e) a linker peptide consisting of the amino acid sequence (GGGGA)₂GGGGS (SEQ ID NO:8);
(f) a linker peptide consisting of the amino acid sequence (GGGGQ)₂GGGGS (SEQ ID NO:5);
(g) a linker peptide consisting of the amino acid sequence (GGGPS)₂GGGGS (SEQ ID NO:6); and
(h) a linker peptide consisting of the amino acid sequence GGGGS(PGGGS)₂ (SEQ ID NO:7).

18. The binding molecule of claim 9, wherein the Fc moiety is an Fc region.

19. The binding molecule of claim 9, wherein the Fc moiety is an scFc region.

20. The binding molecule of claim 9, wherein the binding molecule is a bispecific molecule.

21. The binding molecule of claim 9, wherein the scFv moiety comprises a VH and a VL region, wherein the VH and VL region are genetically linked by a linker peptide comprising the amino acid sequence (GGGGA)₄ (SEQ ID NO:13).

22. The polypeptide of claim 2, wherein the linker peptide is genetically fused to an Fc moiety.

23. The polypeptide of claim 2, wherein the linker peptide is interposed between two polypeptide domains, wherein at least one of the polypeptide domains comprises a VH domain, a VL domain, a scFv molecule, an Fc moiety, a receptor or extracellular domain thereof, an Fab, and a receptor binding portion of a ligand, an enzyme, a growth factor, an interleukin, a cytokine, or a chemokine.

24. The polypeptide of claim 22, wherein the Fc moiety is an Fc region.

25. The polypeptide of claim 22, wherein the Fc moiety is an scFc region.

26. The polypeptide of claim 2, wherein the polypeptide is a bispecific antibody molecule.

27. A composition comprising the polypeptide of claim 2 and a pharmaceutically acceptable carrier.

* * * * *